(12) United States Patent
Gokay et al.

(10) Patent No.: US 10,717,056 B1
(45) Date of Patent: Jul. 21, 2020

(54) METHOD AND APPARATUS FOR PURIFICATION OF CANNABINOID EXTRACTS

(71) Applicants: Michael Cem Gokay, Centerville, OH (US); Kaan Brian Gokay, Centerville, OH (US)

(72) Inventors: Michael Cem Gokay, Centerville, OH (US); Kaan Brian Gokay, Centerville, OH (US)

(*) Notice: Subject to any disclaimer, the term of this patent is extended or adjusted under 35 U.S.C. 154(b) by 0 days.

(21) Appl. No.: 16/565,053

(22) Filed: Sep. 9, 2019

(51) Int. Cl.
*B01F 3/04* (2006.01)

(52) U.S. Cl.
CPC ..................................... *B01F 3/04* (2013.01)

(58) Field of Classification Search
CPC ....................................................... B01F 3/04
See application file for complete search history.

(56) References Cited

U.S. PATENT DOCUMENTS

| | | |
|---|---|---|
| 4,789,554 A | 12/1988 | Scavone et al. |
| 6,485,688 B1 | 11/2002 | Sivavec et al. |
| 6,943,692 B2 | 9/2005 | Castner et al. |
| 7,025,992 B2 | 4/2006 | Whittle et al. |
| 8,980,941 B2 | 3/2015 | Hospodor |
| 9,034,395 B2 | 5/2015 | Whittle et al. |
| 9,155,767 B2 | 10/2015 | Hospodor et al. |
| 9,340,475 B2 | 5/2016 | Mona, III et al. |
| 9,358,259 B2 | 6/2016 | Hospodor et al. |
| 9,732,009 B2 | 8/2017 | Raber et al. |
| 9,861,609 B2 | 1/2018 | Winnicki et al. |

(Continued)

FOREIGN PATENT DOCUMENTS

| | | |
|---|---|---|
| GB | 635121 | 4/1950 |
| WO | 2007141718 | 12/2007 |

(Continued)

OTHER PUBLICATIONS

Abattis Bioceuticals, "New Technology Could Massively Increase the Efficiency of Cannabinoid Extraction", Analytical Cannabis, Dec. 18, 2017, obtained from https://www.analyticalcannabis.com/news/new-technology-could-massively-increase-the-efficiency-of-cannabinoid-extraction-295528 (pp. 1-4).

(Continued)

*Primary Examiner* — Robert A Hopkins
(74) *Attorney, Agent, or Firm* — Daniel F. Nesbitt; Hasse & Nesbitt LLC

(57) ABSTRACT

A process for purifying an extracted material extracted from a biomass material, providing a raw extracted material comprising an amount of a solvent or an extractable compound, heating the raw extracted material to a temperature sufficient to provide and maintain a flowable form, and to raise the partial pressure of the solvent or the extractable compound, increasing the surface area of the raw extracted material, passing a purifying gas across the increased surface area of the raw extracted material, to remove solvent and the extractable compound into the purifying gas to produce a stripped extract material, exposing the stripped extract material to a vacuum pressure to remove residual purifying gas, solvent, and the extractable compound to produce a first-stage purified extract material, and repeating one or more times to prepare a purified extract material.

21 Claims, 15 Drawing Sheets

(56) References Cited

U.S. PATENT DOCUMENTS

| | | |
|---|---|---|
| 9,895,404 B1 | 2/2018 | Baskis |
| 9,937,218 B2 | 4/2018 | Towle |
| 9,983,182 B2 | 5/2018 | Chen et al. |
| 10,004,684 B2 | 6/2018 | Whittle et al. |
| 10,155,708 B2 | 12/2018 | Roura |
| 2004/0147767 A1 | 7/2004 | Whittle et al. |
| 2004/0238745 A1 | 12/2004 | Pedersen et al. |
| 2011/0162951 A1 | 7/2011 | Berry et al. |
| 2013/0337477 A1 | 12/2013 | Kuhr et al. |
| 2014/0287068 A1 | 9/2014 | Lewis et al. |
| 2016/0213624 A1 | 7/2016 | Lindeman |
| 2017/0020944 A1 | 1/2017 | Towle |
| 2018/0078874 A1 | 3/2018 | Thomas |
| 2018/0280459 A1 | 10/2018 | Eyal |
| 2019/0038995 A1 | 2/2019 | Tucker |
| 2019/0077781 A1 | 3/2019 | Dijkstra |
| 2019/0160393 A1 | 5/2019 | Marshall et al. |
| 2019/0328806 A1* | 10/2019 | Rapp .................. B01D 11/0219 |

FOREIGN PATENT DOCUMENTS

| | | |
|---|---|---|
| WO | 2013165251 | 11/2013 |
| WO | 2016022936 | 2/2016 |
| WO | 2018023164 | 2/2018 |
| WO | 2018150182 | 8/2018 |
| WO | 2019023803 | 2/2019 |

OTHER PUBLICATIONS

Bickler, Bob, "How can I rapidly remediate THC from CBD in my hemp extract using flash column chromatography?", Biotage Flash Purification Blog, Jul. 10, 2018, obtained from http://www.flash-purification.com/how-can-i-rapidly-remediate-thc-from-cbd-in-my-hemp-extract-using-flash-column-chromatography/ (pp. 1-8).

Christophersen AS, "Tetrahydrocannabinol stability in whole blood: plastic versus glass containers", Journal of Analytical Toxicology, Jul. 1986, vol. 10 No. 4, p. 129-131 (abstract only).

Gilson ®, "Centrifugal partition chromatography's new use: medical marijuana", Nature Research—Custom Media (Advertisement), available Sep. 8, 2019, retrieved from https://www.nature.com/articles/d42473-018-00066-4 (pp. 1-8).

Layton, Catharine et al., "Forced Degradation of Cannabidiol", Waters Corporation, Aug. 2016, obtained from https://www.waters.com/webassets/cms/library/docs/720005766en.pdf (pp. 1-6).

Molnar, Anna et al., "Recovery of spiked Δ9 -tetrahydrocannabinol in oral fluid from polypropylene containers", Forensic Science International, Apr. 2013, vol. 227 Nos. 1-3, p. 69-73 (abstract only).

Ruppel, Timothy, et al., "Cannabis Analysis: Potency Testing Identification and Quantification of THC and CBD by GC/FID and GC/MS", PerkinElmer Inc., obtained Jun. 25, 2019 from https://www.perkinelmer.com/libraries/APP_Cannabis-Analysis-Potency-Testing-Identifification-and-Quantification-011841B_01 (pp. 1-6).

\* cited by examiner

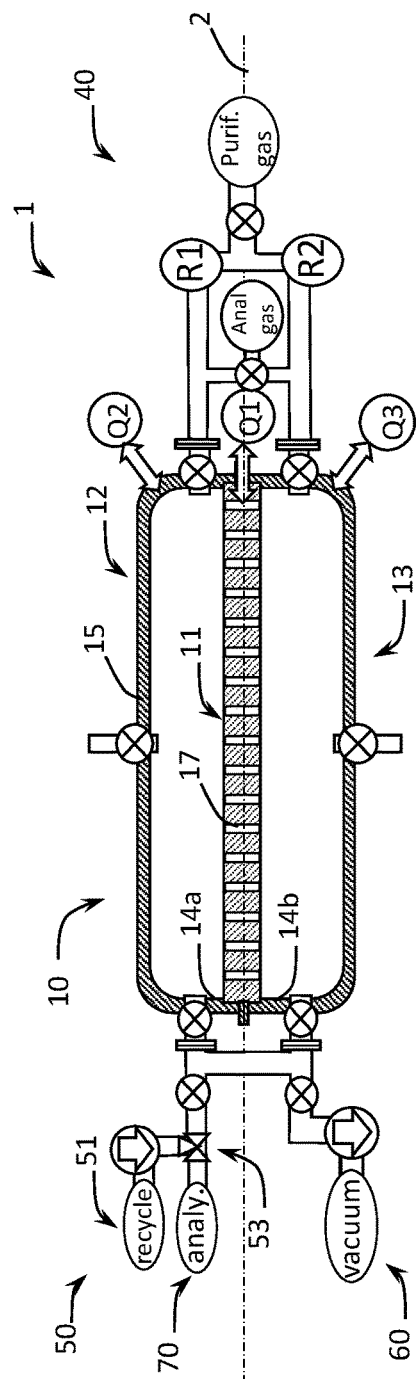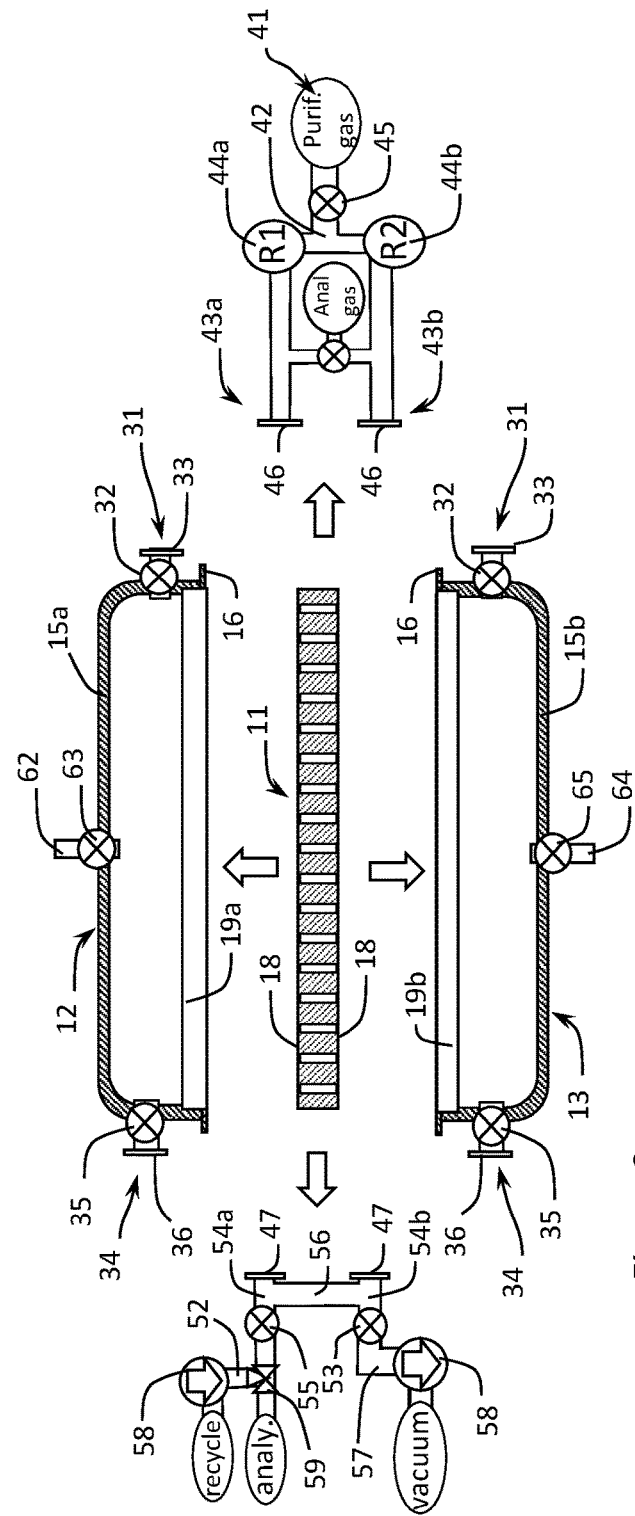
Figure 1
Figure 2

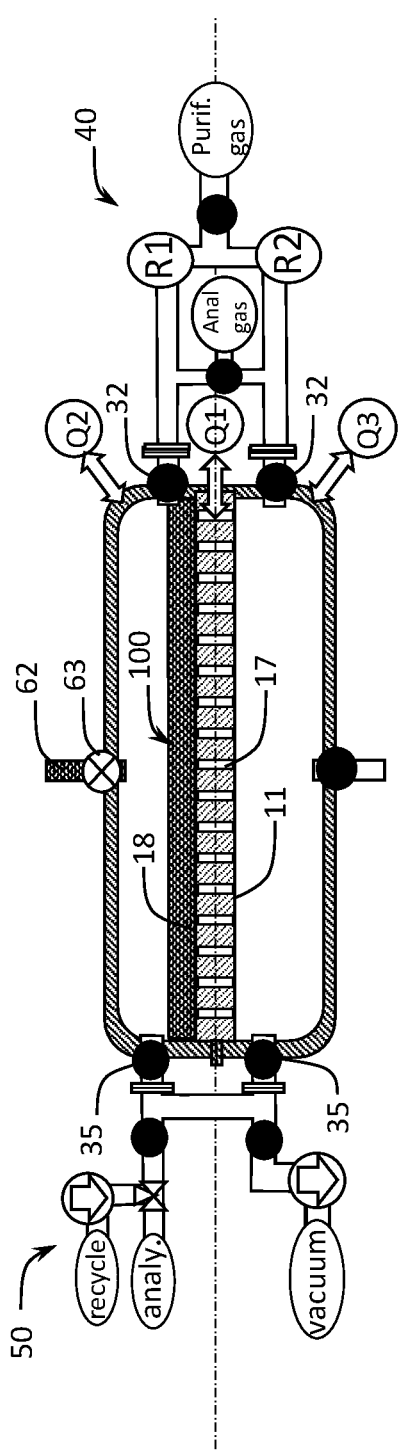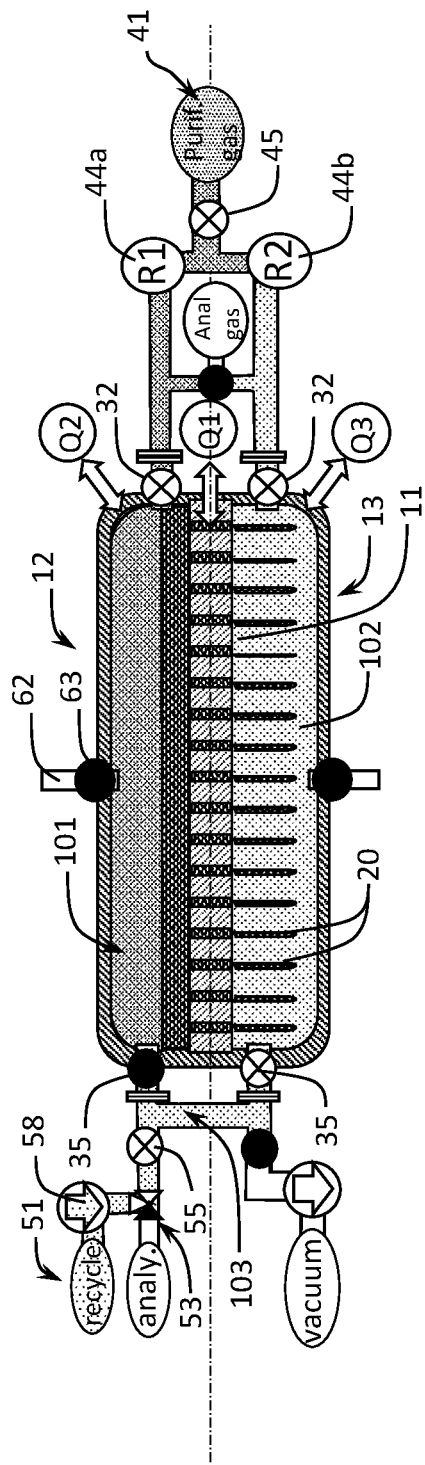
Figure 3
Figure 4

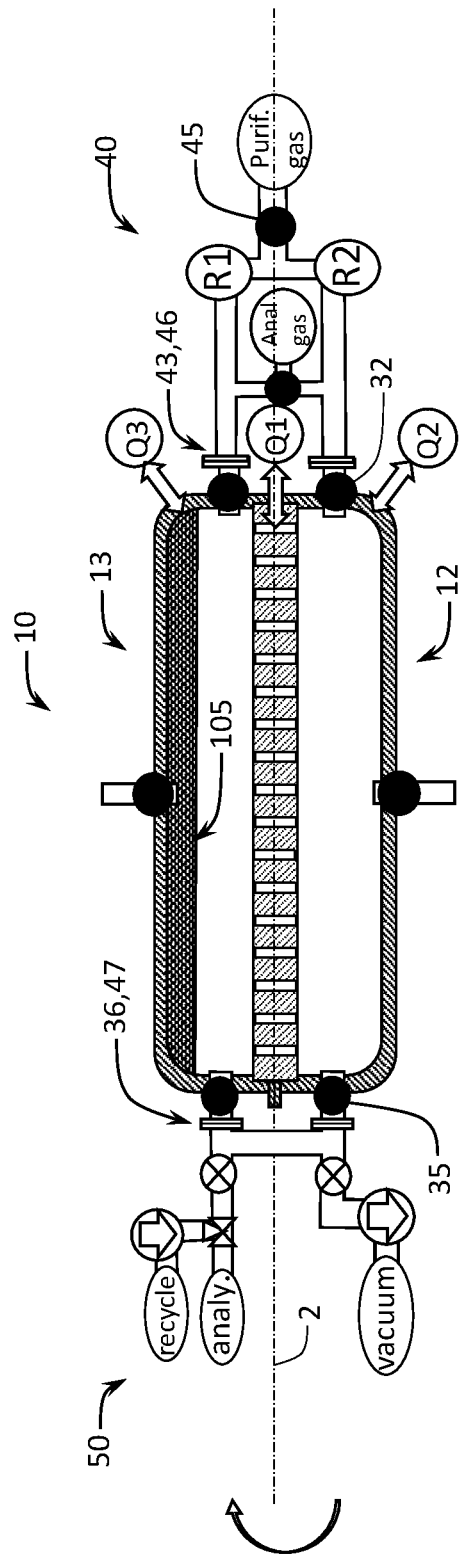
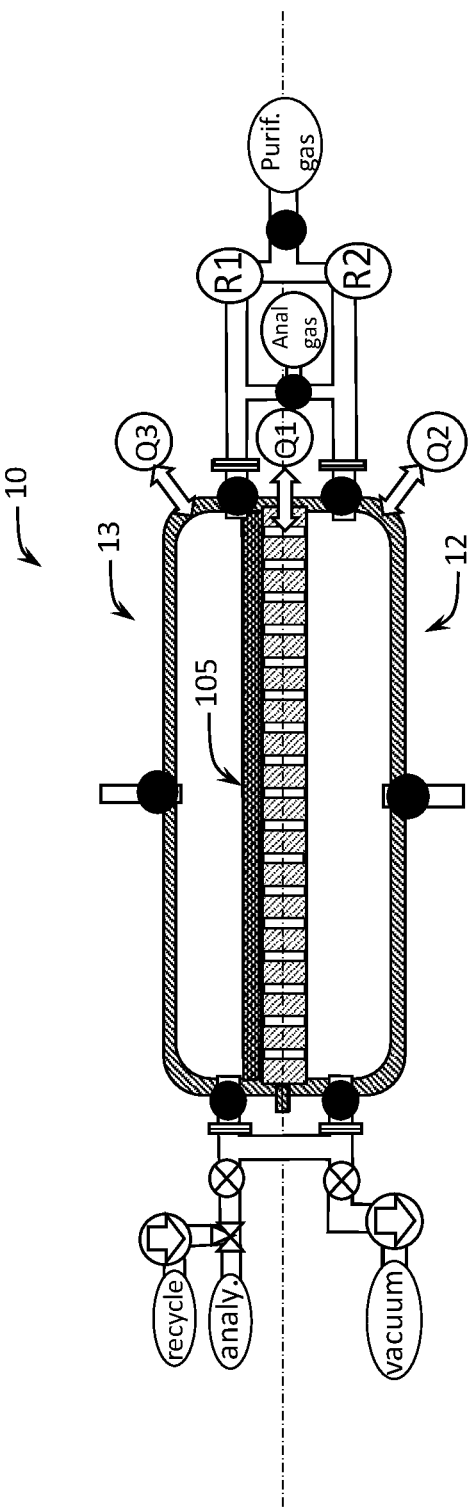
Figure 9
Figure 10

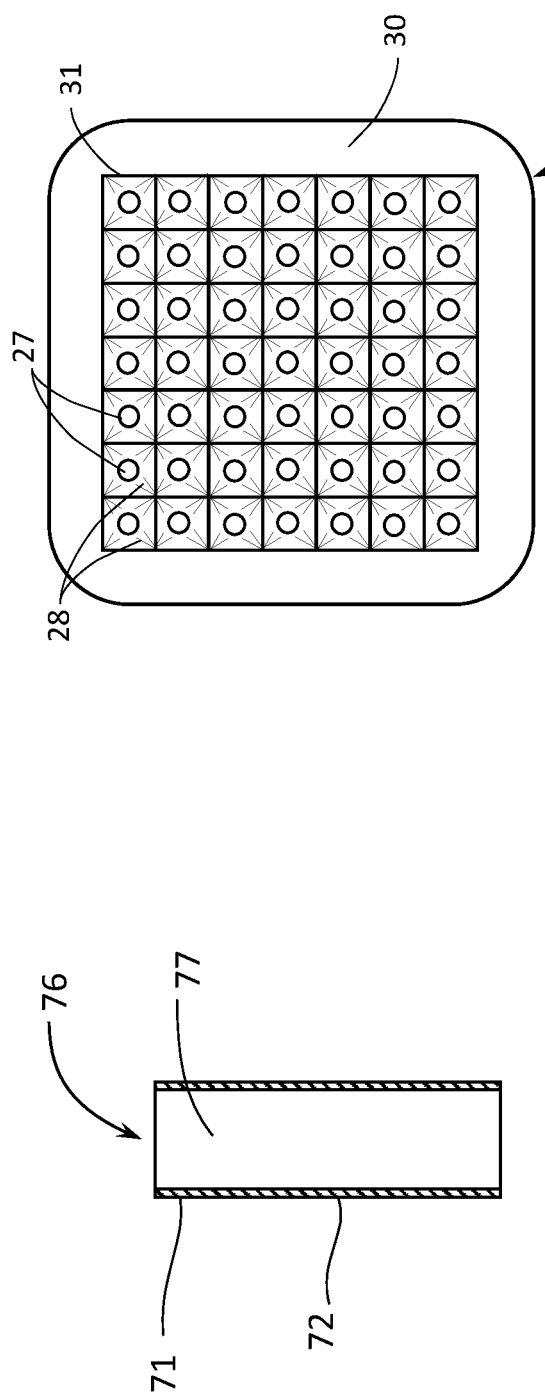
Figure 11H
Figure 12
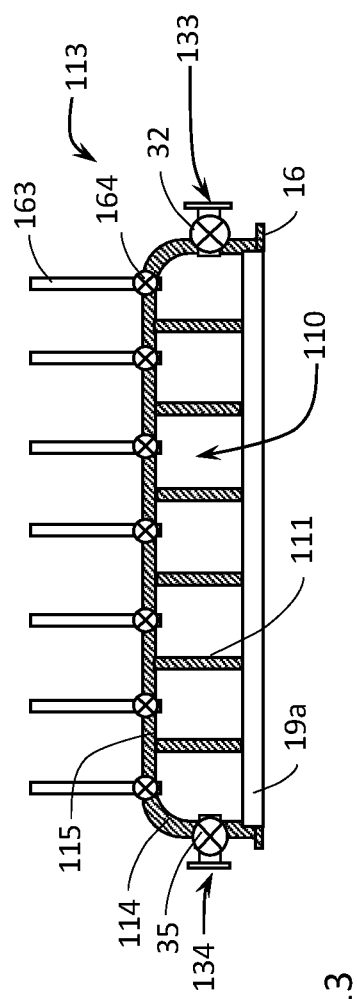
Figure 13

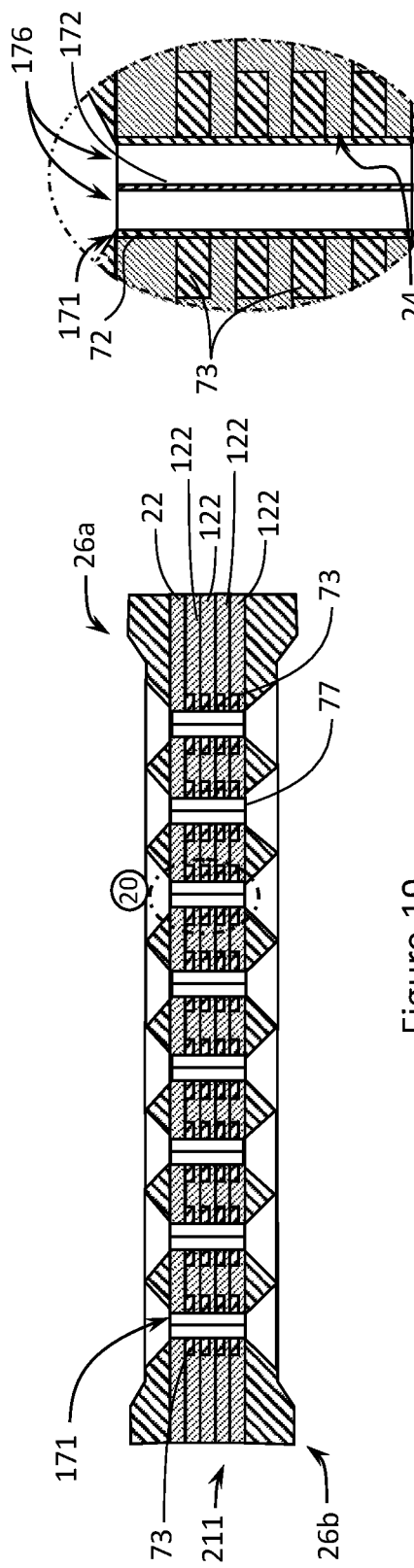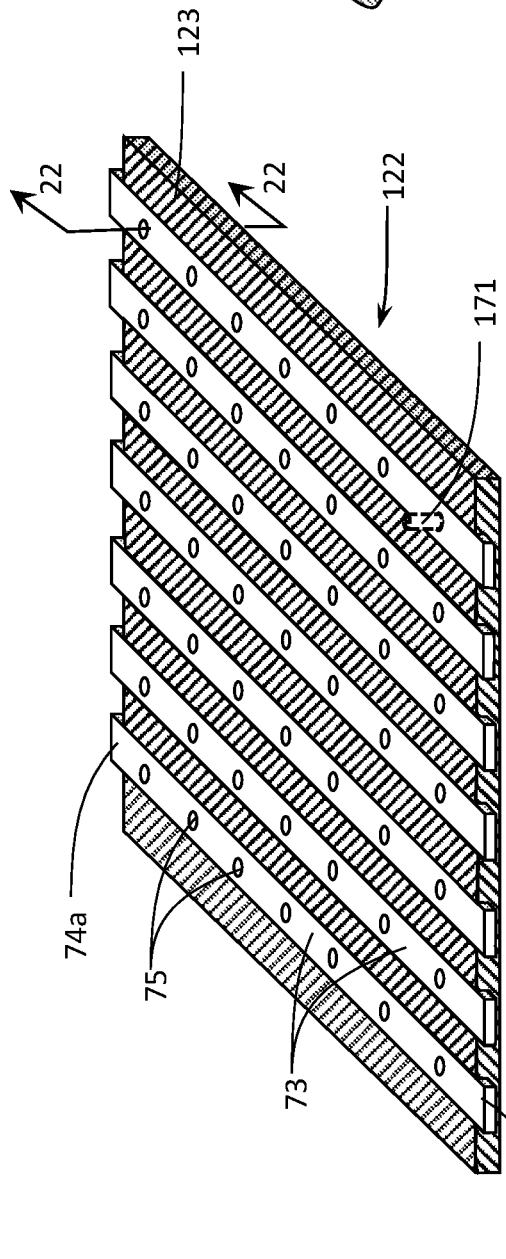

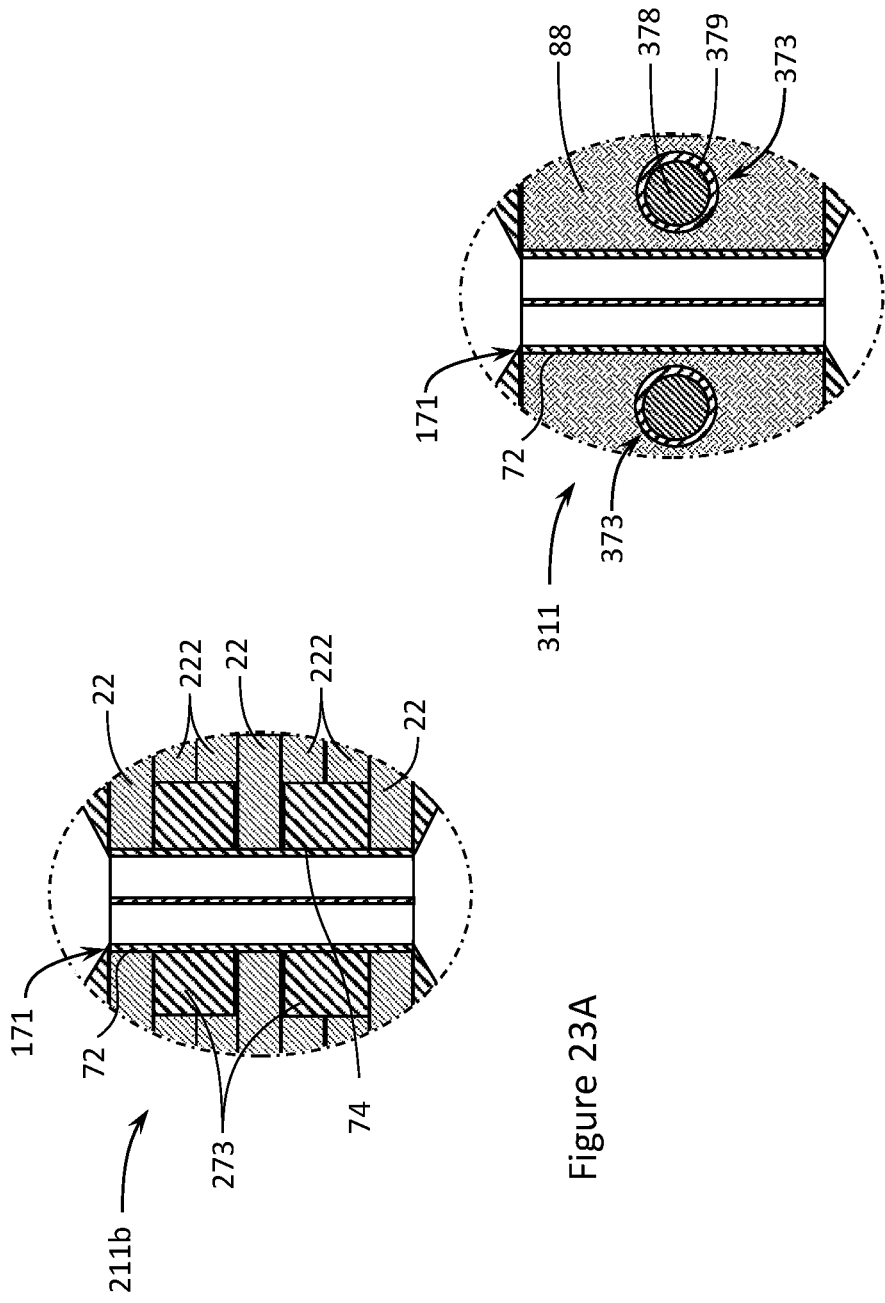

METHOD AND APPARATUS FOR PURIFICATION OF CANNABINOID EXTRACTS

FIELD OF THE INVENTION

The present invention relates to a system and process for purifying cannabinoid extracts.

BACKGROUND OF THE INVENTION

Recent market analysis reports indicate United States sales reaching as much as $100 billion in *Cannabis* and cannabinoid-based products in ten (10) years.

This year US Federal government is growing the largest crop of research in five years, responding to interest in varieties with high levels of tetrahydrocannabinol (THC) and cannabidiol (CBD). The crop will be divided between high THC and high CBD varieties, with recent interest in CBD as a potential medicine for a number of medical conditions. THC is the main psychoactive compound in marijuana that gives the high sensation, while CBD lacks psychoactive activity.

Whole plant oil derived from the *Cannabis* plant, on the other hand, is made from the buds/flower of the female marijuana plant and is comprised of many different cannabinoids including THC, CBD, CBN, and more, in addition to terpenes and other compounds. Whole-plant *Cannabis* oil is not the same as "hemp seed oil." Hemp seed oil is a cold-pressed oil made from the seeds of the hemp plant. It is rich with essential fatty oils and is used mostly for its nutritional benefits and can be bought in health food stores.

*Cannabis* concentrates, commonly referred to as *Cannabis* extracts, are significantly more potent than your standard *Cannabis* buds. Their applications as medicine have proven to be effective for patients suffering from all sorts of ailments. When made properly, a *Cannabis* concentrate is reminiscent of the *Cannabis* strain it was extracted from; the smell, taste, and effects are simply magnified due to a larger concentration by weight.

U.S. Pat. No. 9,034,395 (Whittle et al.) teaches a process for preparing an extract from a natural product which comprises contacting the natural product with a heated gas at a temperature which is greater than 100° C. and sufficient to volatilize one or more constituents of the natural product but does not cause pyrolysis of the natural product thereby volatizing one or more constituents of the natural product to form a vapor, and condensing the vapor to form an extract. U.S. Pat. No. 9,358,259 (Hospodor et al.) teaches a system for recycling a liquid solvent in the solvent extraction of cannabinoids from a *Cannabis* biomass. U.S. Pat. No. 9,937,218 (Towle) teaches a process for purifying *Cannabis* by extracting crude *Cannabis* with ethyl acetate to yield a *Cannabis* extract; dewatering the *Cannabis* extract, consisting essentially of contacting the *Cannabis* extract with a solid dewa-tering agent selected from the group consisting of sodium sulfate, magnesium sulfate and silica; filtering the extract from the solid dewatering agent to yield a dewatered extract; and distilling the dewatered extract to remove a majority of the ethyl acetate, thereby creating the purified *Cannabis* extract. US Patent Publication 2004/0147767 teaches a process for preparing an extract from a natural product which comprises contacting the natural product with a heated gas at a temperature which is greater than 100° C. and sufficient to volatilize one or more constituents of the natural product but does not cause pyrolysis of the natural product thereby volatizing one or more constituents of the natural product to form a vapor, and condensing the vapor to form an extract. US Patent Publication 2018/0078874 teaches a method of extraction of plant oils from plant material by contacting the plant material with a heated gas and/or heated surface of a specific temperature such that the oils contained within the plant material are caused to volatilize and leave the plant material in the form of a vapor, which is condensed and collected using a collection solvent, preferably ethanol or a mixture of ethanol and water, and separating the captured plant oils from the collection solvent to obtain a substantially purified plant oil extract. US Patent Publication 2019/0077781 teaches a process for obtaining a cannabinoid extract from *Cannabis* plant material comprising providing a dispersion of material comprising cannabinoids derived from one or more *Cannabis* plants in an oil, and isolating at least a portion of said cannabinoids from said dispersion to obtain a cannabinoid extract. The disclosures of U.S. Pat. Nos. 9,034,395, 9,358,259, and 9,937,218, and US Patent Publications 2004/0147767, 2018/0078874, and 2019/0077781, are incorporated by reference in their entireties.

A focus of the present invention relates to an improved apparatus and process, for extracting active elements from *Cannabis* and hemp plant (biomass) material, to improve the purity and homogeneity, and to effect and control the active levels to meet broader market needs while addressing current and future legal and regulatory requirements.

SUMMARY OF THE INVENTION

The present invention provides a process for purifying a raw extract material. In an embodiment of the invention, the raw extract material comprises a raw cannabinoid extract material in a bulk amount (for example a 50-grams lot, with scalability to process many kilograms). In another embodiment, the raw but particulate-filtered cannabinoid extract material contains a residual solvent that had been used to prepare the raw cannabinoid extract material from a *Cannabis* or hemp biomass. The methods of the present invention can be used to improve the homogeneity of the treated and purified extracts. The methods of the present invention can also be used to remove selected targeted compounds and other components from the extract, for achieving consistent or preselected target levels of active compounds in the treated or purified extracts. Non-limiting examples of a targeted component that can be removed from an extract material can include one or more terpenes, and one or more active compounds, for example, one or more cannabinoid compounds, including a compound selected from the group consisting of THC, CBD, and CBN, and a combination thereof.

The present invention provides a process for purifying an extracted material that has been extracted from a biomass material, comprising the steps of: a) providing a raw extracted material comprising an amount of a solvent or an extractable compound; b) heating the raw extracted material to a temperature sufficient to provide and maintain a flowable form, and to raise the partial pressure of the solvent or the extractable compound, c) processing the raw extracted material to increase the surface area of the amount of the raw extracted material; d) passing a flow of a purifying gas across the increased surface area of the raw extracted material, to remove at least one of the solvent and the extractable compound from the raw extracted material and into the flow of the purifying gas, resulting in a stripped extract material; e) optionally processing the stripped extracted material to increase the surface area of the amount of the stripped extracted material; f) exposing the stripped extract material to a vacuum pressure that is sufficient to remove at least one of a residual purifying gas contained within the stripped extract material, and the at least one solvent or extractable compound, resulting in a first-stage purified extract material; and g) repeating steps c) through f) on the first-stage purified extract material, one or more times, to prepare a purified extract material.

In an embodiment, the invention can also provide a process for purifying a cannabinoid extract composition comprising one or more cannabinoid compounds, for removing from the cannabinoid extract composition, one or more volatile extraction solvents, one or more cannabinoid compounds, one or more terpenes, or a combination thereof. The process comprises the steps of: a) providing a mass of a raw cannabinoid extract composition comprising one or more cannabinoid compounds and/or an initial concentration of at least one volatile extraction solvent; b) passing the mass of the raw cannabinoid extract composition through a porous partition to form a plurality of streams of the raw cannabinoid extract composition; c) exposing the plurality of streams of the raw cannabinoid extract composition to a stream of a purifying gas, to pass an amount of the one or more cannabinoid compounds and/or volatile extraction solvent contained within the mass of the raw cannabinoid extract composition into the stream of the purifying gas, thereby forming a second mass of the cannabinoid extract composition; d) exposing the second mass of the raw cannabinoid extract composition to a vacuum environment, to pass a second amount of the one or more cannabinoid compounds and/or volatile extraction solvent contained within the second mass of the raw cannabinoid extract composition into the vacuum environment, thereby forming a further mass of the cannabinoid extract composition; e) repeating steps a) through d) one or more additional times, thereby forming a purified cannabinoid extract composition having a reduced concentration of the at least one volatile extraction solvent and/or one or more cannabinoid compounds.

The removing from the cannabinoid extract composition of one or more volatile extraction solvents, one or more cannabinoid compounds, and/or one or more terpenes, can be performed in a series of steps or stages in which a single compound or a mixture of compounds are removed in a step or stage from the cannabinoid extract composition. The removal of a single compound or a mixture of compounds in a step or stage from the cannabinoid extract composition can depend on the processing conditions selected.

A process of the present invention also provides an apparatus with which a process of the invention can be performed. The apparatus includes a vessel that can withstand both vacuum and pressure conditions, that can provide surfaces for the heating of the extract materials to controlled temperatures up to 400 degrees C., and which can process the extract materials to increase the surface area of the amount of the raw extracted material, and preferably to process the extract materials into thin films, particulates (droplets), or streams of material to increase the removal of solvents and other extractable compounds, which can include, but are not limited to, one or more of cannabidiol (CBD), tetrahydrocannabinol (THC), cannabinol (CBN), and terpenoids, from the extract materials.

The present invention provides a heated dual-chamber vessel and an apparatus for use in purifying an extracted material that has been extracted from a *Cannabis* or hemp biomass material. The process of the present invention, using the heated dual-chamber vessel and apparatus described herein, can effectively reduce residual extraction solvents and volatile, extractable compounds, and especially CBD and THC, to selective and predetermined levels, which can be determined using periodic analyses of the treated or purified extract material in subsequent staged process steps. The process and apparatus provide a purified extract material that is compositionally homogenous and analytically consistent and reproducible.

The heated dual-chamber vessel includes a porous partition that divides the vessel into a first chamber vessel and a second chamber vessel, each of the first chamber vessel and a second chamber vessel comprising peripheral wall having distal rim that defines an opening into the respective chamber vessel, and an base wall that defines a closed end of the respective chamber vessel, wherein the first chamber vessel and a second chamber vessel can be sealed along together at the respective distal rims to form a pressure- and vacuum-sealed vessel. The porous partition comprises a rigid structure having a multiplicity of passages extending between the opposed outer faces of the porous partition, which passages place the first chamber and the second chamber into fluid communication. Each of the first chamber vessel and the second chamber vessel include at least one, and typically a plurality of ports disposed in either or both the peripheral sidewall and base wall, and a plurality of shutoff valve to selectively open and close the plurality of ports.

The present invention also provides an apparatus for use in a process of the invention, the apparatus including the heated dual-chamber vessel, a gas delivery system, and a gas recovery system. Other elements of the apparatus and system can include a trap for volatiles or extractable compounds, and an online High Performance-Liquid-Chromatography (HPLC) equipment that can identify the identity and levels of major cannabinoids from the *Cannabis* or hemp plant biomass material and in the treated, extracted or purified extract material.

The gas delivery system includes a supply of a pressurized extraction purifying gas, and associated piping, valving and control devices, for each of the first chamber vessel and a second chamber vessel, independently or jointly, for shutting off and turning on the pressurized purifying gas, and regulating the mass flow rate, pressure, and the temperature of the pressurized purifying gas, that flows through the respective chamber vessel.

The gas recovery system includes a collection and recycle system for a low-pressure gas, including a low-pressure volatile-laden purifying gas, and associated piping, valving and control devices, for each of the first chamber vessel and a second chamber vessel, independently or jointly, for closing off and passing the low-pressure volatile-laden purifying gas, and a condenser to capture condensable fluids from the low-pressure volatile-laden purifying gas. The gas recovery system can also include a vacuum system that communicates fluidly with each of the first chamber vessel and a second chamber vessel, independently or jointly, and associated piping, valving and control devices, and a condenser to capture condensable fluids from the vacuum flow.

The dual-chamber vessel can include a means for rotating the vessel around a central axis in order to switch the respective positions of the first chamber vessel and the second chamber vessel. In one embodiment, the connections between the gas delivery system and the gas recovery system with the vessel can comprise pairs of quick-connection couplings that mate and connect the ports of the vessel with the piping of the gas delivery system and the gas recovery system, to facilitate disconnecting, rotating, and reconnecting the vessel. In an embodiment, the connections can also be made employing high-temperature flexible lengths of vacuum/pressure tubing and joints to facilities rotation without having to disconnect the couplings.

The apparatus can also include at least one material port disposed in the base wall either or both the first chamber vessel and the second chamber vessel, for introducing or withdrawing, fluid materials, including a raw extract material or a purified extract material, into or from, the chamber vessels.

An example of another apparatus for use in performing the process of the present invention is a wiped film evaporator (WFE).

BRIEF DESCRIPTION OF THE DRAWINGS

FIG. 1 shows an apparatus for use in a process for purifying a cannabinoid extract composition.

FIG. 2 shows the apparatus of FIG. 1, including an extraction vessel having an upper chamber vessel, a lower chamber vessel, a gas supply system, and gas recovery and vacuum systems, in exploded configuration.

FIG. 3 shows the apparatus of FIG. 1 with a raw extract material loaded into the upper chamber vessel of the apparatus.

FIG. 4 shows the heated extract material being gas pressurized in the upper chamber vessel and passed through passageways of a porous partition and into the lower chamber vessel of the apparatus.

FIG. 9 shows the extraction vessel 10 inverted to place the chamber vessel with the purified extract material as the upper chamber vessel.

FIG. 10 shows the extraction vessel of FIG. 9 reconnected with the gas supply system and the gas recovery and vacuum systems.

FIG. 11H shows an insert port useful in the porous partition of FIG. 11C.

FIG. 12 shows a plan view of the porous partition assembly of FIG. 11G.

FIG. 13 shows a chamber vessel can having a multi-port chamber vessel.

FIG. 19 shows a heated porous partition having a plurality of resistive heat elements.

FIG. 20 shows a passageway and resistive heat elements of the heated porous partition of FIG. 19.

FIG. 21 shows a conductive partition plate having a planar base made of an electrically-insulative material, and a plurality of elongated, resistive heat elements extend slots in the planar base.

FIG. 22 shows sectional view of a heated passageway of the conductive partition plate of FIG. 21.

FIG. 23A shows another embodiment of a conductive partition plate.

FIG. 23B shows yet another embodiment of a conductive partition plate.

DETAILED DESCRIPTION OF THE INVENTION

Figure 5:
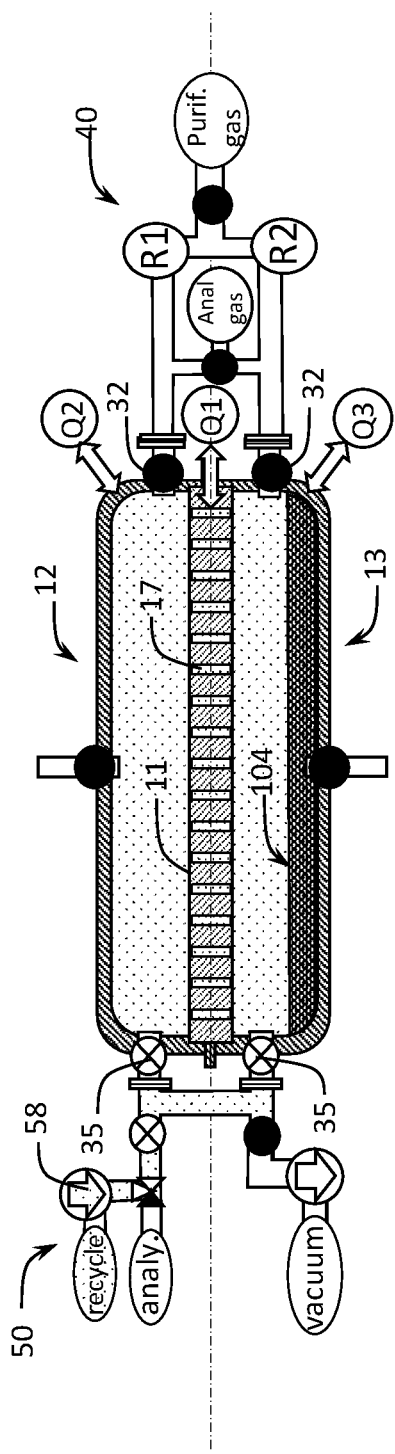
FIG. 5 shows a layer of first-stripped purified extract material in the lower chamber vessel, while the gas in the upper chamber vessel is vented.

FIGS. 1 and 2 show an apparatus for use in a process for purifying a cannabinoid extract composition by removing one or more volatile extraction solvents and/or one or more volatile active compounds from the cannabinoid extract composition. The apparatus 1 includes a dual chambered vessel 10 that includes a porous partition 11 that divides the vessel 10 into a first chamber vessel 12 and a second chamber vessel 13. FIG. 2 shows the first chamber vessel 12, the second chamber vessel 13, and the porous partition 11 in a vertically exploded arrangement. The vessel 10 has a peripheral wall 14 and opposed base walls 15 that define closed ends of the vessel 10. In an embodiment of the invention, the size of the first and second chamber vessels 12,13 are of the same size and dimensions, though in other embodiments the size and shape of either can be different. Each of the first chamber vessel 12 and the second chamber vessel 13 have an opposed base wall 15$a$,15$b$ and a peripheral sidewall 14$a$,14$b$ having a distal rim that defines an open end. The respective rims of the first and second chambers 12,13 include a peripheral flange 16 that defines a peripheral seal 17 between the respective open ends of the first chamber vessel 12 and the second chamber vessel 13. The first chamber vessel 12 and the second chamber vessel 13 are separable sealing elements and can be positioned by independent means with respect to one another, which can include manual positioning, or positioning robotically or mechanically, and controlled automatically or manually.

In a typical embodiment, an apparatus 1 can have a physical height and a diameter (or equivalent diameter-based plan view dimension) that can each independently be at least 10 cm, up to about 2 meters, depending on the volume or mass of the initial raw extract material.

In an embodiment, the porous partition 11 comprises a rigid structure having a plurality, and typically a multiplicity, of pores or through passages 17, extending between the opposed outer faces 18 of the porous partition 11, and placing the first chamber 12 and the second chamber 13 into fluid communication. In an embodiment, a passage 17 can have a uniform, straight-through passageway. The multiplicity of passages 17 can a diameter or equivalent cross-section size of at least 1 micron, which can be any one of at least 10 microns (0.01 mm), at least 0.05 mm, at least 0.1 mm, at least 0.2 mm, at least 0.3 mm, at least 0.4 mm, and at least 0.5 mm; and a size of not more than 2 mm, which can be any one of not more than 1.5 mm, or not more than 1 mm, or not more than 0.5 mm, or not more than 0.25 mm, or not more than 0.1 mm. The passages 17, individually or collectively, can be a regular in shape, such as circular, elliptical or polygonal, or irregular in shape.

Figure 11A:
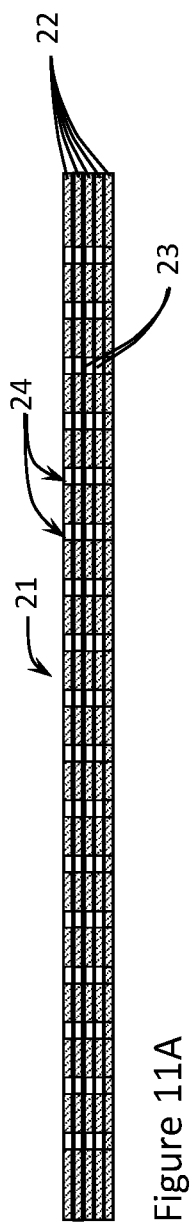
FIG. 11A shows a porous partition having a plurality of stacked plates, each plate having a multiplicity of passageways.
Figure 11B:
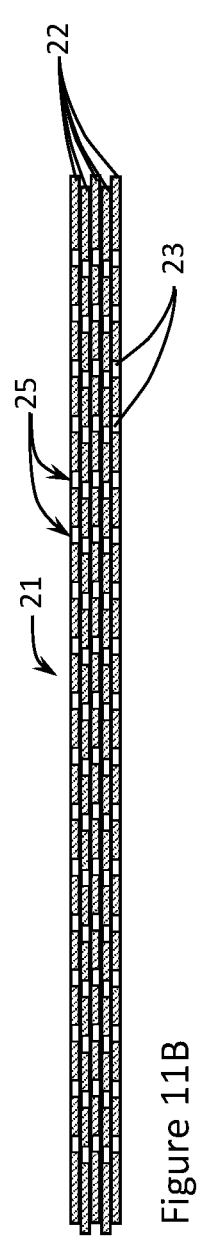
FIG. 11B shows the porous partition of FIG. 11A with passageways axially offset from either or both passageways of adjacent stacked plates to form the non-linear, offset passageways.

In an alternative embodiment shown in FIG. 11A, a porous partition can be a variably-porous partition 21 comprising a plurality of stacked plates 22, each plate 22 have a plurality or a multiplicity of pores or bores 23, where corresponding or overlapping pores 23 of the plurality of stacked plates 22 form a corresponding passageway 24. In a related embodiment shown in FIG. 11B, the overlapping pores 23 can be axially offset from either or both overlapping pores 23 of adjacent stacked plates 22, to form the non-linear, offset passageways 25. In some embodiments, the plurality of pores 23 are the same size, while in other embodiments, the plurality of pores 23 can have different or varying size, within a plate or plate-to-plate. Providing an offset passageway can increase the linear length of the path of the passageway 25, providing an increase in the time to which the extract material is exposed to the plates 22. This can be important when heating the extract material through the porous partition, as described hereinbelow.

A suitable material for a portion or component of a porous partition 11 or 21 that contacts the extract material can be a non-toxic resilient material, non-limiting examples of which are aluminum and stainless steel.

Figure 11C:
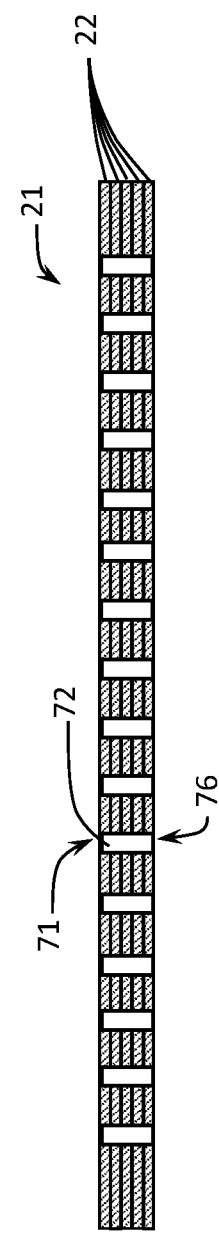
FIG. 11C shows a porous partition of FIG. 11A having insert ports inserted secured within the plurality of passageways.

In another embodiment of the invention, illustrated in FIG. 11C, the porous partition 21b includes a plurality of insert ports 71 that are inserted through and secured within the plurality of passageways 24. The insert port 71 consists of a cylindrical wall 72 that is fitted into the passageway 24 of the porous partition 21b and has a through passage 76 through which the extract material can passes. The use of the insert ports 71 allows control of the material that contacts the heated extract material and allows the use of any material within the remaining body of the porous partition, without regard to its interaction with the extract material. In some embodiments of an insert port, the through passage 76 can be subdivided into two or more sub-passages 176, defined by one or more interior fin walls 172 extending along the axial length of the cylindrical wall 72 and connect between the inner surface of the cylindrical wall 72, as illustrated in FIG. 20.

Figure 11D:
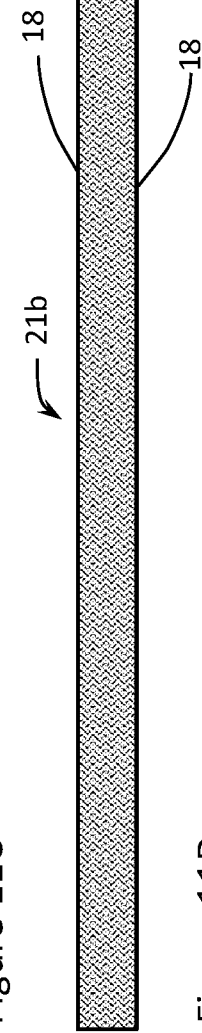
FIG. 11D shows a porous partition comprised of a metal foam material.
Figure 11E:
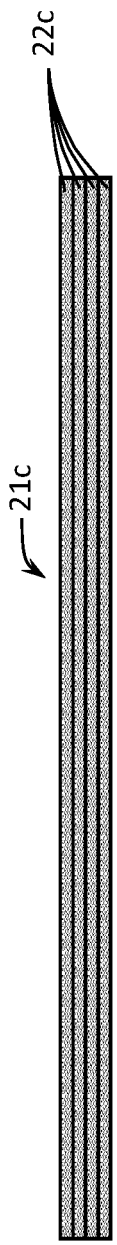
FIG. 11E shows a porous partition having a plurality of stacked metal foam plates.

In an alternative embodiment, the porous partition can comprise a metal foam partition 21c, shown in FIG. 11D, that is made of a suitable material, having a multiplicity of open-cell pores that form an interconnected network, extending between the opposed surfaces 18 of the metal foam partition 21c. The suitable material can include, without limitation, aluminum and stainless steel. In another embodiment, a metal foam partition 21d can comprises a plurality of stacked metal foam plates 22c, shown in FIG. 11E. The multiplicity of passages through the porous foam partition are typically irregular and highly random in cross-sectional and pathway shape, having equivalent cross-section size as described herein above for porous partitions.

A porous partition (including but not limited to porous partitions 11, 21, 21a, 21b, 21c and 21d) is positioned between the first chamber vessel 12 and the second chamber vessel 13. In the illustrated embodiment, each of the first chamber vessel 12 and the second chamber vessel 13 include a respective peripheral frame 19a,19b, and the porous partition 11 is held within and between the respective peripheral frames 19a,19b. In some embodiments, the periphery of the porous partition 11 is sealed within each peripheral frame 19a,19b.

Figure 11F:
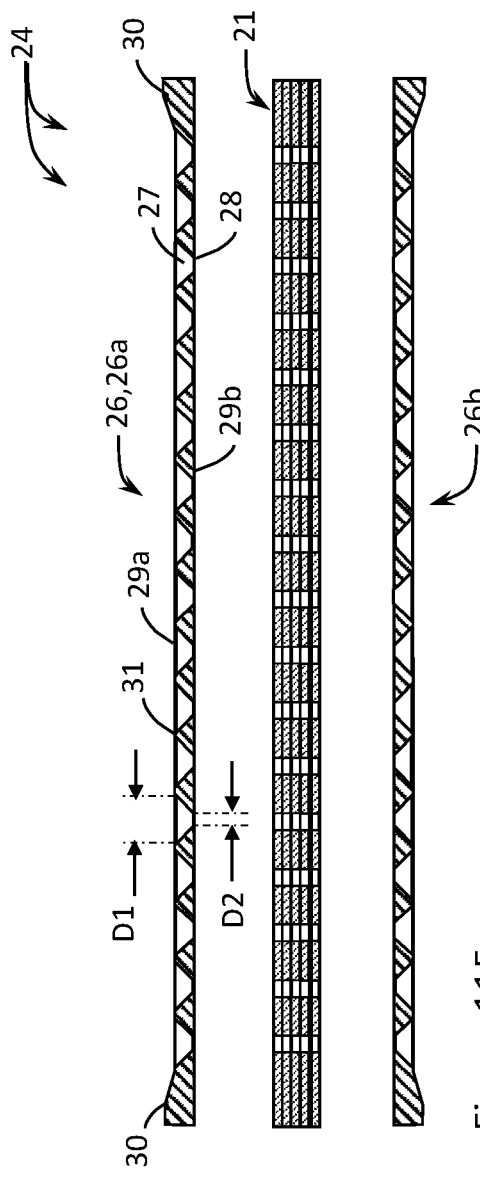
FIG. 11F shows a porous partition for assembly with a pair of opposed funneling trays for directing the flowable extract material toward and into the passageways.
Figure 11G:
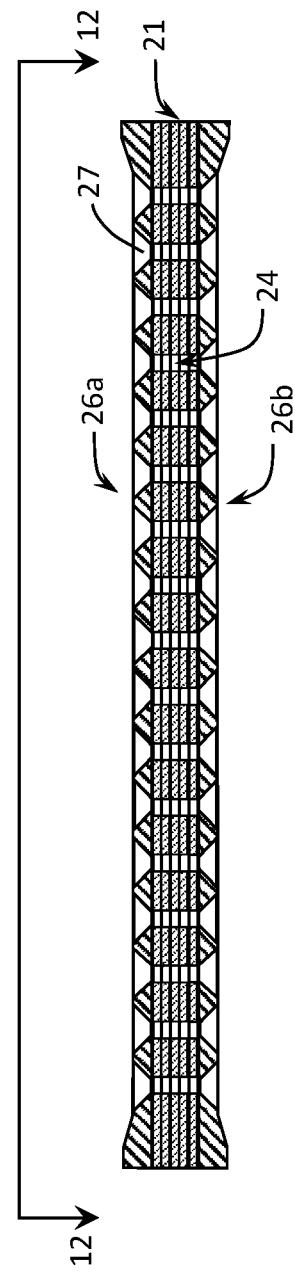
FIG. 11G shows a porous partition assembly of FIG. 11F.

In some embodiments, a porous partition can be combined with a funneling tray 26, disposed on both (or either) surfaces 18 of the porous partition 21, as illustrated in FIGS. 11F and 11G, to provide a means for directing the flowable extract material toward and into the respective passageways 24 with which they are aligned, to help ensure rapid and complete directing of the flowable extract material through the porous partition. Each funnel tray 26a,26b includes a planar body having a peripheral area 30, and a plurality of tapered surfaces that define a through hole 27 that extends from a larger, square-shaped opening tapering from the outer surface 29a, through and toward a smaller, circular opening 28 in the inner surface 29b. The size of the smaller opening 28 in the inner surface 29b can be the same as the passageway 24 in the porous partition 21, though can also be of a larger size that can circumscribe two or more openings to passageways 24. The typical ratio of the diameter (or effective size) of D1, the larger opening of the tapered through hole 27, to D2, the smaller hole 28, is about 1.5:1 to about 3:1. In some embodiments, the larger, opening of the through hole can be a circular shape or other shape, and the smaller, circular opening can be square or other shape, with the through hole 27 having a conical shape. The thickness of the funnel tray 26 can be any thickness needed to provide sufficient and proper funneling of the bulk extract material to the selected passageway(s) 24 with minimal or no residual extract remaining in the upper chamber vessel. A funnel tray 26a,26b positioned on both outer surfaces 18 of the porous partition 21 provides the funnel means when either of the first chamber vessel 12 and the second chamber vessel 13 are in the upper position, relative to the other. FIG. 12 illustrates in a plan view a 7×7 rectangular array porous partition, where the plurality of tapered through holes 27 can be arranged with minimal upper surface 31 (essentially, an edge line) between adjacent conical-shaped through holes 27, with sufficient peripheral area 30 for forming a sufficient seal with the peripheral frame 19a,19b of the respective first chamber vessel 12 and the second chamber vessel 13.

In a preferred embodiment, the material has good heat transfer properties for applying heat and changing the temperature of the extract material as it enters and passes through the porous partitions. The invention includes a heated porous partition and a method of heating the extract material passing through the porous partition to an elevated temperature. In an embodiment of the invention, the porous partition includes a means for providing heat input Q1 into the porous partition 11 to heat the extract material rapidly and "just in time" to an elevated temperature to improve (raise) volatility of the one or more target compounds, including one or more active compounds, in the extract material being treated. The heat input means can be accomplished using, without limitation, an electromotive force, a heat exchange fluid, and an irradiated energy source.

In an embodiment shown in FIGS. 19-22, a resistive heat element is used to pass heat though an insert port that lines each of the passageways of the porous partition. FIG. 19 shows a cross sectional view of a heated porous partition 211 that includes a plurality of conductive partition plates 122. Each conductive partition plate 122 includes a planar base 123 made of an electrically-insulative material, and having a plurality of elongated columns of slots 124 extending in parallel and each traversing a row of apertures 125 formed through the slot 124, as shown in FIGS. 21 and 22. A plurality of elongated, resistive heat elements 73 extend along each of the slots 124, across the entire width (length) of the planar base 123. Each resistive heat element 73 has a plurality of apertures 173 along the length that register with an aperture 125 in one of the slots 124 to form a plurality of heated passageways 75 in each conductive partition plate 122. Each resistive heat element 73 is made of an electrically-conductive material, selected without limitation from a group consisting of aluminum, aluminum alloys, and ferrous alloys. Each aligned series of passageways 75 in a stack of the conductive partition plates 122 define a plurality of passageways 24, each passageway 24 retaining and constraining an insert port 171. As shown in FIG. 20, each insert port 171 includes a cylindrical wall 72 that defines an opening that communicates between the opposed upper and lower sides of the heated porous partition 211. An outer surface of the cylindrical wall 72 of the insert ports 171 is configured to contact the wall 174 defining each opening 173 in the resistive heat elements 73, shown in FIG. 22, placing each insert port 171 into thermal communication with the wall 174 of the resistive heat element 73.

In the illustrated embodiment, each insert port 171 comprises one or more interior fin walls 172 extending along the axial length of the cylindrical wall 72, subdividing the through passage 76 into two or more sub-passages 176.

A plurality of conductive partition plates 122 are sandwiched in a stack forming the porous partition 211. In the illustrated embodiment, four conductive partition plates 122 are placed in a stack, with slots 124 in the electrically-insulative planar base 123 insulating electrically each resistive heat element 73, thereby providing four heat generating sources along the length of each insert port 171. A non-conductive partition plate 22 is placed over the top of the uppermost conductive partition plate 122 to electrically insulate the porous partition from the vessel and the funnel trays 26a,26b. The non-conductive partition plate 22 has series of opening openings 23 arranged in rows and columns, corresponding and registering with each of the opening 173 along each resistive heat element 73 and across the plurality of resistive heat element 73.

In an embodiment of the invention, an electromotive force is applied across opposed ends 74a and 74b of each resistive heat element 73, heating each resistive heat element 73 along its length and consequently, raising the temperature along the cylindrical walls 72 of the insert ports 171. The physical design and location of heating sources Q1 offers sufficient heat transfer capability for heating and raising the temperature of each stream of extract material passing through the porous partition to a predetermined and selectable temperature. During the processing of extract material flowing through the passageways 176, an electromotive force can be applied across each of the four resistive heat elements 73, to correspondingly heat and raise the temperature of each insert port 171, and the extract material passing therethrough. The electromotive force applied across the four resistive heat elements 73 can be the same value or can be of different values. The effect of the heating from the resistive heat elements 73 is to raise the temperature of the extract material to a target temperature only as the extract material passes through the passageways 176, and just prior to exiting of the extract material in streams 20, as illustrated in FIG. 4.

In another embodiment shown in FIG. 23A, the resistive heat elements can include pairs of vertically-aligned resistive heat elements 273 extend across the entire width (column) of the porous partition 211b, for each of the rows of insert ports 171. Each pair of vertically-aligned resistive heat elements 273 has a row of openings defined by a circular wall 274, configured to contact the outer surface of the cylindrical wall 72 of the insert ports 171, placing each insert port 171 into thermal communication with the wall 274 of the resistive heat elements 273. Each pair of vertically-aligned resistive heat elements 273 is separated and electrically insulated by a non-conductive partition plate 22 placed both over the top and under each resistive heat element 273, and surrounded and restrained laterally by a pair of non-conductive securing plate 222.

In another embodiment shown in FIG. 23B, the resistive heat elements can include pairs of horizontally-opposed resistive heat elements 373 extend across the entire width (column) of the porous partition 311, for each of the rows of insert ports 171. Each pair of horizontally-aligned resistive heat elements 373 extend along opposite sides of each row of insert ports 171, is separated and electrically insulated by a non-conductive partition plate 22 placed both over the top and under each resistive heat element 273, and surrounded and restrained laterally by a pair of non-conductive securing plate 222. Each resistive heat element 373 includes an elongated thermally- and electrically-conductive core 378, surrounded along the length by a thermally conductive, electrically-insulative coating 379, to electrically isolate the resistive heat elements 373 from the porous partition 311. The porous partition 311 consists of a solid, continuous, thermally-conductive plate 88 having the thickness and other dimensions of the porous partition 311. Alternatively, the porous partition can consist of a stack of thermally conductive plates, of the dimensions of the continuous plate 88. The thermally-conductive plate 88 can be either electrically insulative, or electrically conductive and electrically separated from each electrically-conductive core 378 by the electrically-insulative coating 379. Non-limited examples of the material of the continuous plate 88 can include aluminum and aluminum alloys.

Each of the first chamber vessel 12 and the second chamber vessel 13 include at least one, and typically a plurality of ports disposed in the sidewalls 14a,14b and opposed base walls 15a,15b, respectively. Returning to the illustrated embodiment shown in FIGS. 1 and 2, the first chamber vessel 12 includes at least one gas inlet port 31 that includes a shutoff valve 32 to selectively open and close the gas inlet port 31, and at least one gas outlet port 34 that includes a shutoff valve 35 to selectively open and close the port 34. The second chamber vessel 13 includes at least one gas inlet port 31 that includes a shutoff valve 32 to selectively open and close the gas inlet port 31, and at least one gas outlet port 34 that includes a shutoff valve 35 to selectively open and close the port 34.

A gas delivery system 40 includes a supply 41 of a pressurized purifying gas, a gas piping system 42, and a shutoff valve 45 that communicates the purifying gas supply 41 with the gas supply piping 42. The gas supply piping 42 includes a first supply port 43*a* and a second supply port 43*b*, and a first gas pressure regulator 44*a* and second gas pressure regulator 44*b* to regulate the pressure and/or flow of purifying gas from the gas supply piping 42 to the respective first supply port 43*a* and a second supply port 43*b*, respectively. The first supply port 43*a* is configured to communicate fluidly and connect sealingly to the at least one gas inlet port 31 of the first chamber vessel 12, and the second supply port 43*b* is configured to communicate fluidly and connect sealingly to the at least one gas inlet port 31 of the second chamber vessel 13.

A gas recovery system 50 includes a collection and recycle system 51 for a low-pressure gas, including a low-pressure purifying gas, and a gas return piping 52 that communicates fluidly the collection and recycle system 51 with the vessel 10. A selectable diversion valve 53 can connect the gas return piping 52 to either the collection and recycle system 51 or an analytical system 70. A condenser 58 in the piping between the selectable diversion valve 53 and the collection and recycle system 51, captures condensable liquids from a gas stream passing to the collection and recycle system 51. The gas return piping 52 converges from a divided piping 56, each end of which communicates fluidly to the first recovery ports 54*a* and 54*b*, respectively. The first recovery port 54*a* is configured to communicate fluidly and connect sealingly to the at least one gas outlet port 34 of the first chamber vessel 12, and the second supply port 54*b* is configured to communicate fluidly and connect sealingly to the at least one gas outlet port 34 of the second chamber vessel 13. A shutoff valve 55 is disposed between the diversion valve 53 and the divided piping 56.

An extraction solvent can include one or more of the following volatile solvents: ethanol and ethanol solution; ethyl acetate solution; one or a mixture of propane, butane, pentane and hexane; and carbon dioxide. A purifying gas can include one or more reducing or inert gases that can include nitrogen, argon, carbon dioxide and helium, a non-oxidizing gas that can include steam. An analytical gas can include an inert gas, preferably argon or helium.

The gas recovery system 50 also includes a vacuum system 60 that communicates fluidly with the divided piping 56 through a vacuum piping 57 and includes a condenser 58 in the vacuum piping 57 to capture condensable fluids from the vacuum flow. A shutoff valve 59 is disposed between the condenser 58 and the divided piping 56.

In the embodiments of the invention, the various shutoff valves can be operated manually or remotely, under human or automated control.

The apparatus 1 can include a means for rotating the vessel 10 around a central axis 2 in order to switch the respective positions of the first chamber vessel 12 and the second chamber vessel 13. In one embodiment, after disconnecting from the gas delivery system 40 and the gas recovery system 50, the vessel 10 is configured to rotate while the gas delivery system 40 and the gas recovery system 50 remain stationary. The means for rotating can include a mechanized apparatus, typically motorized, for rotating the vessel 10 around the central axis 2 employing a suitable axle and bearings. The means for rotating can be operated manually or remotely, under human or automated control.

In some embodiments, a pair of quick-connection couplings 46 mate and connect the first supply port 43*a* and the second supply port 43*b*, respectively, the gas delivery system 40 to a corresponding pair of quick-connection couplings 33 of the gas inlet ports 31 of the respective first chamber vessel 12 and the second chamber vessel 13. A pair of quick-connection couplings 47 mate and connect the first recovery port 54*a* and the second recovery port 54*b*, respectively, the gas recovery system 50, to a corresponding pair of quick-connection couplings 36 of the gas outlet ports 34 of the respective first chamber vessel 12 and the second chamber vessel 13. The mating quick-connecting couplings are configured to be actuated or maneuvered under control between a connected, sealed position, and a disconnected position. Before the vessel 10 is rotated between positions, the mating quick-connecting couplings are actuated from the connected, sealed position, to the disconnected position. After the vessel 10 has been rotated 180 degree, the re-oriented, mating quick-connecting couplings are re-connected and sealed.

The apparatus 1 can include at least one material port 62 disposed in the base wall 15*a* of the first chamber vessel 12 for either introducing a fluid form of a raw extract material into the vessel 10 or withdrawing a fluid form of a purified extract material from within the vessel 10. A shutoff valve 63 selectively opens and closes the material supply port 62. It is also understood that a raw extract material 100 can also be introduced into the vessel 10 by raising the first chamber vessel 12 from the second chamber vessel 13, placing the raw extract material 100 onto the porous partition 11, and lowering and sealing the first chamber vessel 12 to the second chamber vessel 13.

The apparatus 1 also can include at least one material port 64 disposed in the base wall 15*b* of the second chamber vessel 13 for either introducing a fluid form of a raw extract material into the vessel 10, or withdrawing a fluid form of a purified extract material from the vessel 10, described herein after. A shutoff valve 65 selectively opens and closes each of the one or more material ports 64.

FIGS. 3 through 10 illustrate a process according to the present invention for purifying a raw extract material using the apparatus 1. In an embodiment of the invention, the raw extract material 100 comprises a raw cannabinoid extract material, which is typically filtered to remove but particulate matter. In another embodiment, the raw cannabinoid extract material contains a residual solvent that had been used to prepare the raw cannabinoid extract material from a *Cannabis* or hemp biomass.

As illustrated in FIG. 3, a raw extract material 100 is loaded into the vessel 10 through the material port 62 through the opened shutoff valve 63, to a predetermined initial volumetric or mass material amount. In some embodiments, the shutoff valve 63 is opened and the raw extract material 100 is drained or pumped into the first chamber vessel 12 from an outside supply source. The first chamber vessel 12 is initially isolated from the gas delivery system 40 and the gas recovery system 50 by closing shutoff valves 32 and 35. Typically, the initial charge or bulk of raw extract material 100 is heated to a temperature sufficient for flowability, so that the loaded raw extract material 100 spreads over and covers the upper surface 18 of the porous partition 11. Heat Q2 and Q3 is applied to the first chamber vessel 12 and a second chamber vessel 13, respectively, to maintain a predetermined or target bulk temperature or temperature range of the raw extract material 100. In some embodiments, the porous partition 11 is heated via heat source Q1, to a predetermined temperature or within a predetermined temperature range to warm and thin (reduce the viscosity of) the raw extract material 100 passing through the passageways 17 of the porous partition 11 to a temperature sufficient to effect volatility of a residual extraction solvent and/or a volatile target compound in the raw extract material 100.

As illustrated in FIG. 4, the space in the first chamber vessel 12 above the porous partition 11 and the raw extract material 100 disposed thereon, is pressurized with a gas, typically a purifying gas, by opening valve 32 leading from the gas delivery system 40 into the first chamber vessel 12, and actuating the control valve 45 to pass high-pressure purifying gas 101 from the purifying gas supply 41 through the gas supply piping 42, while the downstream pressure of the high-pressure purifying gas pressure with first gas pressure regulator 44a. The purifying gas pressure within the space of the first chamber vessel 12 is regulated to maintain a selected absolute pressure sufficient to force the flowable raw extract material 100 down through the passageways 17 of the porous partition 11, as a target mass rate.

The raw extract material 100 forced down through the multiplicity of small-diameter passageways 17 results in a liquid stream 20 comprising either droplets or a stream or a combination thereof, having an increased specific surface area. The multiplicity of liquid streams 20 results in a significant multiplication of the total surface area of the raw extract material 100 that is exposed to the gas space within the lower, second chamber vessel 13. Concurrently, a lower-pressure purifying gas 102 is passed through the opened shutoff valve 32 into the gas space of the second chamber vessel 13, at a selected, reduced absolute pressure that is controlled by second gas pressure regulator 44b. The lower-pressure purifying gas 101 passes into and through the gas space of the second chamber vessel 13, and out through the opened shutoff valve 35. The flow of the lower-pressure purifying gas 102 is sufficient to pass the low-pressure purifying gas 102 into and through the streams 20 of extract material extruded through the passageways 17 of the porous partition 11, and to carry off volatilized solvent material or other active compound being emitted or volatilized from within and through the surface areas of the multiplicity of streams 20. The temperature, mass flow rate, and absolute pressure of the lower-pressure purifying gas 102 passing through the second chamber vessel 13 is sufficient to strip volatile solvents or other target compounds volatilized from within and through the surface of the streams 20, including a residual extraction solvent, one or more terpenes, and one or more cannabinoid compounds. The exiting lower-pressure purifying gas 103 containing volatile and carried solvent and/or other target compounds passes out of the gas space of the second chamber vessel 13, and into the gas recovery system 50. The lower-pressure purifying gas 103 laden with a volatilized solvent or active compound passes through opened shutoff valve 55 and diverted by the selectable diversion valve 53 to the collection and recycle system 51. Any extraction solvent or active compound contained in the volatile-laden lower-pressure purifying gas 103 is condensed in condenser 58, isolated, and typically recycled, while the resulting volatile-free lower-pressure purifying gas 103 passes from the collection and recycle system 51 to a gas compressor for recovery and storage of the purifying gas at a higher pressure.

After all of the raw extract material 100 has been expressed through the passageways 17 of the porous partition 11 and into the bottom of the second chamber vessel 13 as a layer of first-stripped purified extract material 104, shown in FIG. 5, the gas delivery system 40 is isolated from the vessel 10 by closing off inlet shutoff valves 32 into both the first and second chamber vessels 12 and 13, while the high pressure purifying gas 101 within the first chamber vessel 12 is vented down to ambient pressure into the gas recovery system 50 through opened shutoff valve 35, where any volatile solvents and other volatile material (volatile active compound and/or terpenes) are condensed out of the gas stream in the condenser 58 before the collection and recycle system 51.

Figure 6:
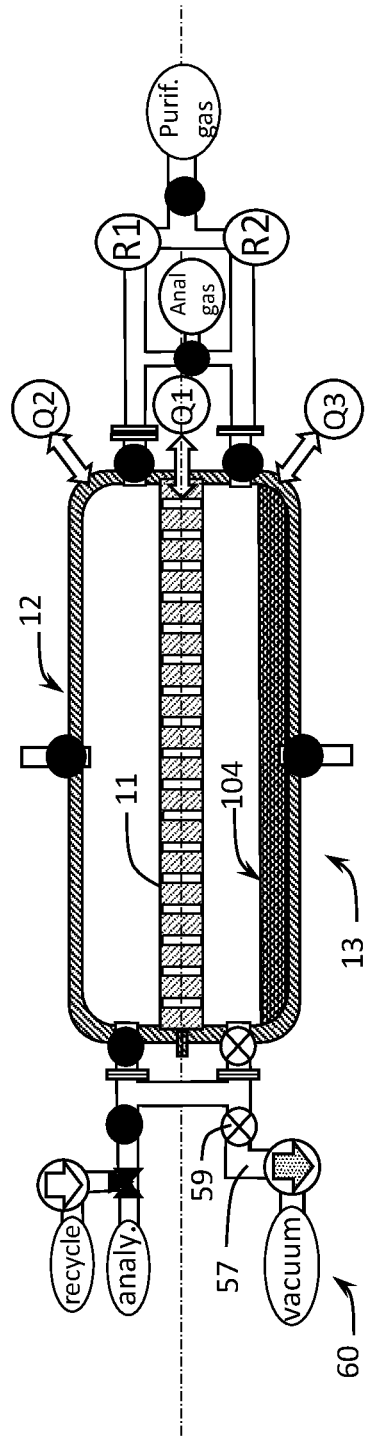
FIG. 6 shows a vacuum being applied onto the layer of first-stripped purified extract material in the lower chamber vessel to produce a first-stage purified extract material.

As shown in FIG. 6, a vacuum from the vacuum system 60 can then be applied onto the layer of first-stripped purified extract material 104 lying on the bottom of the second chamber vessel 13 of the vessel 10, through opened shutoff valve 59 in the vacuum piping 57, and open valve 35 leading to the second chamber vessel 13. The second chamber vessel 13 has been heated (Q3 heat source) to a temperature or a temperature range sufficient both to maintain the flowability of the extract material, and to raise the volatility of any remaining volatile solvent and other volatile materials within the first-stripped purified extract material 104. Typically, the vacuum (absolute pressure) applied to the second chamber vessel 13 by the vacuum system 60 is reduced and maintained down to not more than 10 torr, and more typically between about 0.01 torr and about 1 torr. The reduced absolute pressure in the second chamber vessel 13 effected by the vacuum enhances extraction of residual volatile solvent and other volatile material dissolved or entrained within the first-stripped purified extract material 104. The vacuum is maintained for a time sufficient to remove a quantity of the residual volatile solvent and other volatile material that are condensed and recovered in the condenser 58 and resulting in a first-stage purified extract material 105, shown in FIG. 7.

Figure 7:
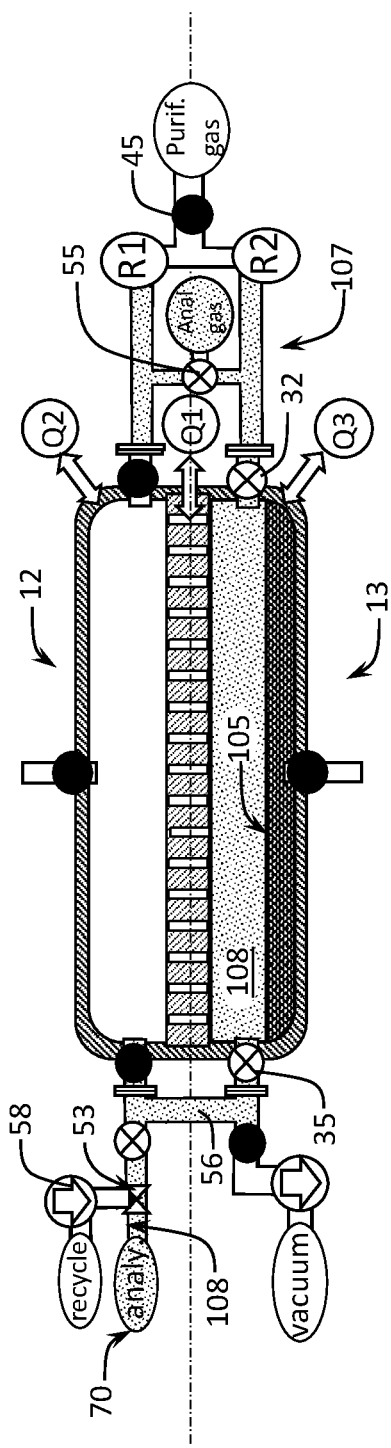
FIG. 7 shows an analytical gas passed across the exposed upper surface of the first-stage purified extract material, for detecting an analytical property of the purified extract material.

In an optional step, a method is provided for detecting an analytical property of the first-stage purified extract material 105. As illustrated in FIG. 7, an analytical gas 107 is passed at a fixed and predetermined flow rate through the gas space of the second chamber vessel 13 and across the exposed upper surface of the first-stage purified extract material 105, to allow a concentration of either volatile solvent or other analytically-detectable volatile, extractable compounds to become entrained or contained within the analytical gas stream 107. The flowing stream 108 of analytical gas with entrained or contained volatile materials exits the gas space in the second chamber vessel 13 and passes through the divided piping 56 and is diverted by the selectable diversion valve 53 to the analytical system 70. The analytical system 70 includes analytical instrumentation capable of detecting the mass or concentration of one or more volatile materials entrained or contained within the volatile-laden analytical gas stream 108. It should be understood that this method can be used for detecting an analytical property of, including an identify and concentration of one or more volatile, extractable compounds contained within, the first-stage purified extract material 105, or in a purified extract material at another stage or step in the apparatus or process, including the raw extract material 100, the first-stripped purified extract material 104, and a purified extract material in later stages of the process.

At the completion of the analytical step, the analytical gas stream 107 is shut off at its control valve 55, and all shutoff valves 32,35 are closed.

Figure 8:
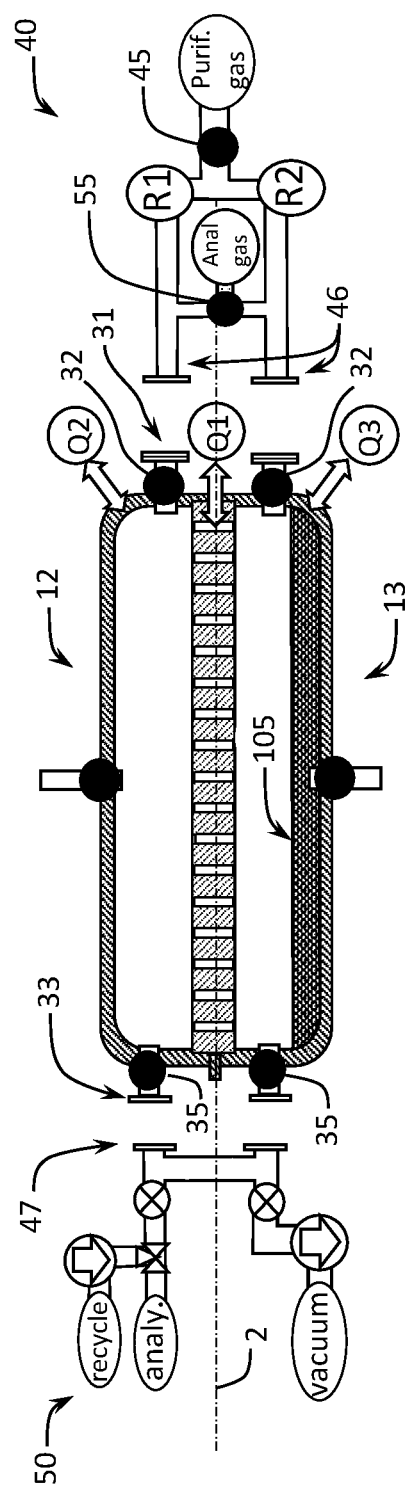
FIG. 8 shows the extraction vessel disconnected from the gas supply system and the gas recovery and vacuum systems.

As shown in FIG. 8, the vessel 10 is then disconnected from the gas delivery system 40 and the gas recovery system 50, as described above at mated quick-connection couplings 46 and 47, and the vessel 10 is rotated about its central axis 2 to invert the second chamber vessel 13 over and above the first chamber vessel 12, shown in FIG. 9, and the vessel 10 is re-connected to the gas delivery system 40 and the gas recovery system 50, via the mated quick-connection couplings 31/46 and 33/47, on respective sides. The Q2 and Q3 heat sources of the first and second chamber vessels 12,13 maintain a flowable temperature. With the second chamber vessels 13 now above and heated by the Q3 heat source, the first-stage purified extract material 105 remains liquid and flowable, and by gravity will drip down and deposit onto the upper surface 18 of the porous partition 11, as shown in FIG. 10.

In an alternative embodiment, not shown though understood by a person of ordinary skill, prior to the application of a vacuum on the first-stripped purified extract material 104, the vessel 10 is disconnected from the gas delivery system 40 and the gas recovery system 50, rotated about its central axis 2 to invert the second chamber vessel 13 (containing the first-stripped purified extract material 104) over and above the first chamber vessel 12, and re-connected to the gas delivery system 40 and the gas recovery system 50, as described above. After the flowable first-stripped purified extract material 104 spreads across the porous partition 11, pressurized purifying gas is introduced into upper second chamber vessel 13 and over the first-stripped purified extract material 104, to force the first-stripped purified extract material 104 down through the passageways 17 of the porous partition 11. A vacuum is applied to the lower first chamber vessel 12, and streams 20 of the first-stripped purified extract material 104 exiting through the passageways of the porous partition 11 are exposed to the vacuum, thereby enhancing extraction of residual volatile solvent and other volatile material dissolved or entrained within the first-stripped purified extract material 104. Once all first-stripped purified extract material 104 has passed through the porous partition 11 and into the lower first chamber vessel 12, the pressurized gas in the upper second chamber vessel 13 can be vented. The vacuum can optionally be maintained on the lower first chamber vessel 12 for an additional time thereafter, producing the first-stage purified extract material 105. The vessel 10 is then disconnected from the gas delivery system 40 and the gas recovery system 50, rotated about its central axis 2 to invert the first chamber vessel 12 (containing the first-stage purified extract material 105) over and above the second chamber vessel 13, and re-connected to the gas delivery system 40 and the gas recovery system 50.

At this stage, the process illustrated in FIGS. 4-10 and described herein can be repeated once or more times until a finished purified extract material is obtained, based on a result of the analytical step or some other recorded metrics.

At the completion of the processing of the extract material in the vessel 10 into a purified extract material, the purified extract material is removed typically by gravity drainage, although in other embodiments the purified extract material can be pumped from within the lower of the two chamber vessels 12,13.

In a first embodiment illustrated in FIG. 13, a chamber vessel can include a multi-port chamber vessel 113, configured with a plurality of material ports 63, illustrated showing seven ports 163 in the sectional view, disposed in the base wall 115. The plurality of material ports 163 provide a means for withdrawing the purified extract material from the vessel 10. In the illustrated embodiments shown in FIGS. 13 and 14, a front elevation view shows seven columns of the material ports 163, where a side elevation view of the multi-port chamber vessel 113 would show seven rows of the material ports 163, providing a total of 49 (7×7) material ports. A separate shutoff valve 164 selectively opens and closes each of the one or more material ports 163. In alternative embodiments, the number of rows and columns can be the same, or different in number, and can independently number 2, 3, 4, 5, 6, 8, 9, 10, or more rows and/or columns.

The multi-port chamber vessel 113 also provides a plurality of full partition walls 111 that divide the gas and purified extract space of the multi-port chamber vessel 113 into a plurality of sub-chambers 110 commensurate with the number of material ports 163. Each partition wall extends from the inner surface of the base wall 115, outwardly to the open end of the multi-port chamber vessel 113, to proximate the peripheral frame 19*a*. Each partition wall 111 forms a peripheral wall surrounding one or more of the passages of the porous partition 11, in order to receive within the sub-chamber 110 an amount or portion of the purified extract material.

Figure 14:
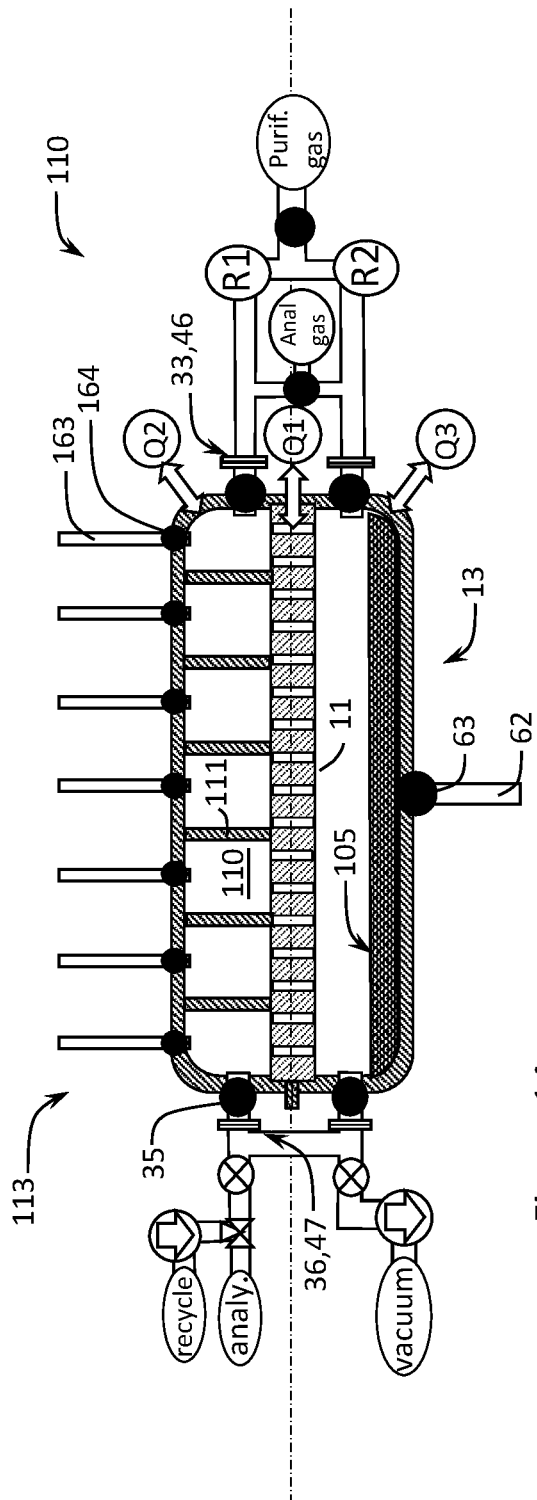
FIG. 14 shows the multi-port chamber vessel in place of the upper chamber vessel 12, with the purified extract material in the lower vessel chamber as shown in FIG. 8.
Figure 15:
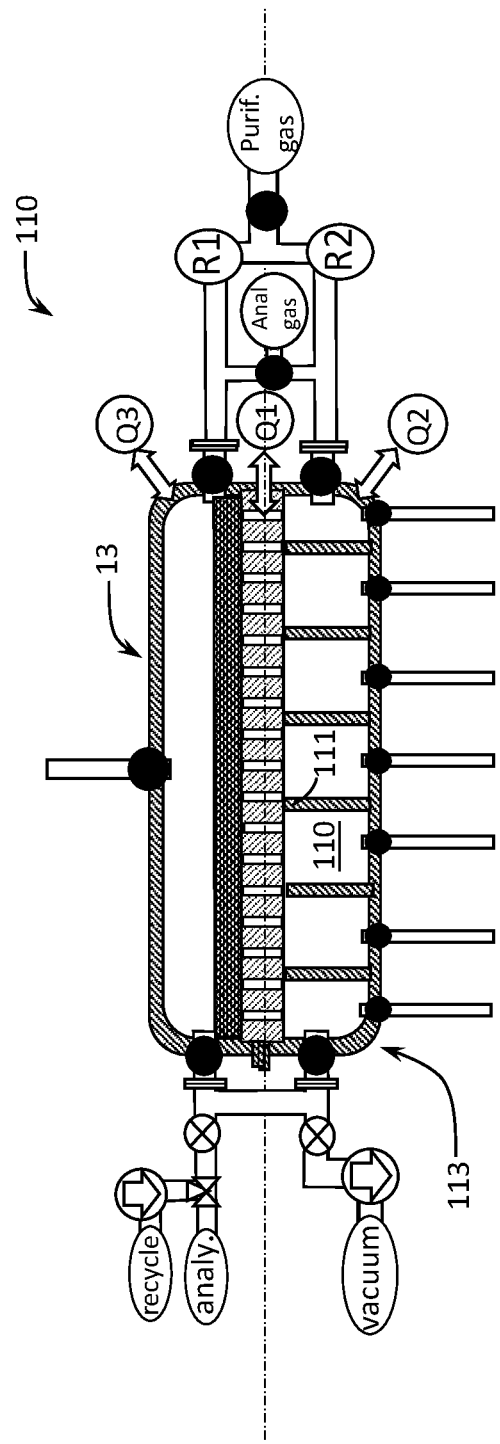
FIG. 15 shows the vessel of FIG. 14 with the multi-port vessel chamber rotated below.

FIGS. 14-17 illustrate the use of the multi-port chamber vessel 113 for dispensing a purified extract material into an equivalent number of containers or single-dose receptacles. FIG. 14 illustrates the multi-port apparatus 110, wherein the multi-port chamber vessel 113 is installed in place of one of the chamber vessels 12,13, and in the illustrated embodiment, in place of the first chamber vessel 12 as shown in FIG. 8. The vessel 110 is then rotated to place the chamber vessel 13 above the multi-port chamber vessel 113, and the vessel 110 re-connected to the gas delivery system 40 and the gas recovery system 50, allowing the flowable purified extract material to drip down by gravity and deposit onto the upper surface 18 of the porous partition 11, as shown in FIG. 15.

Figure 16:
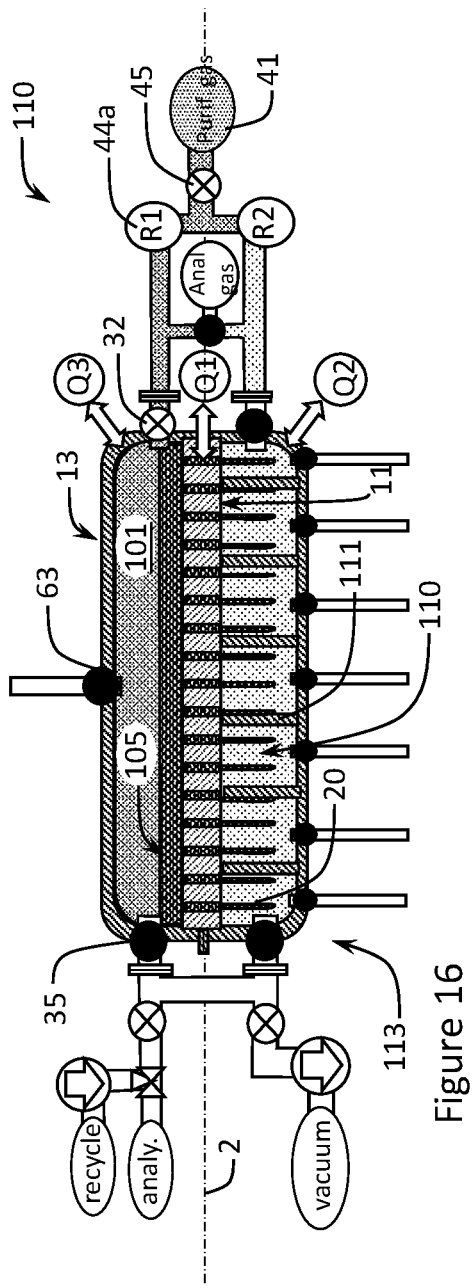
FIG. 16 shows the vessel of FIG. 15 with pressurized gas forcing the purified extract material into the multiple sub-chambers of the multi-port vessel chamber.
Figure 17:
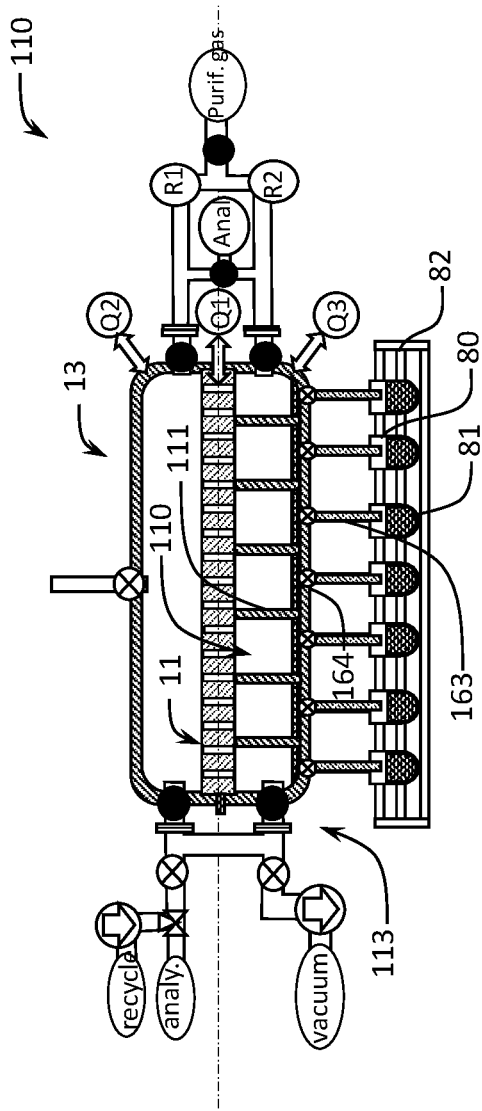
FIG. 17 shows the purified extract material within the sub-chambers being dispensed into a corresponding plurality of receptacles.

To pass the flowable purified extract material into the sub-chambers 110 in the multi-port chamber vessel 113 below, the gas space in the upper second chamber vessel 13 above the porous partition 11 and the purified extract material is pressurized with a gas, typically the purifying gas, by opening valve 32 leading from the gas delivery system 40 into the second chamber vessel 13, and actuating the control valve 45 to pass high-pressure purifying gas 101 from the purifying gas supply 41 through the gas supply piping 42, as shown in FIG. 16. The purifying gas pressure within the space of the second chamber vessel 13 forces the purified extract material down through the passageways of the porous partition 11, and into each respective sub-chamber 110. The purified extract material within the plurality of sub-chambers 110 is then dispensed from each of the plurality of sub-chambers 110 and into a corresponding plurality of receptacles 80 supported in a matrix structure 81 with holding tray 82 as shown in FIG. 17. In an embodiment, the receptacle 80 can comprise a single-dose receptacle, such as a capsule, or a blister cavity in a correspondingly numbered blister pack. The single-dose receptacle can be configured to be covered and sealed after introducing the purified extract material. In some embodiments, the matrix structure 81 can include a cover for sealing the plurality of receptacles 80, to prevent contamination and further loss of volatile components from the contained purified extract material 105.

Figure 18:
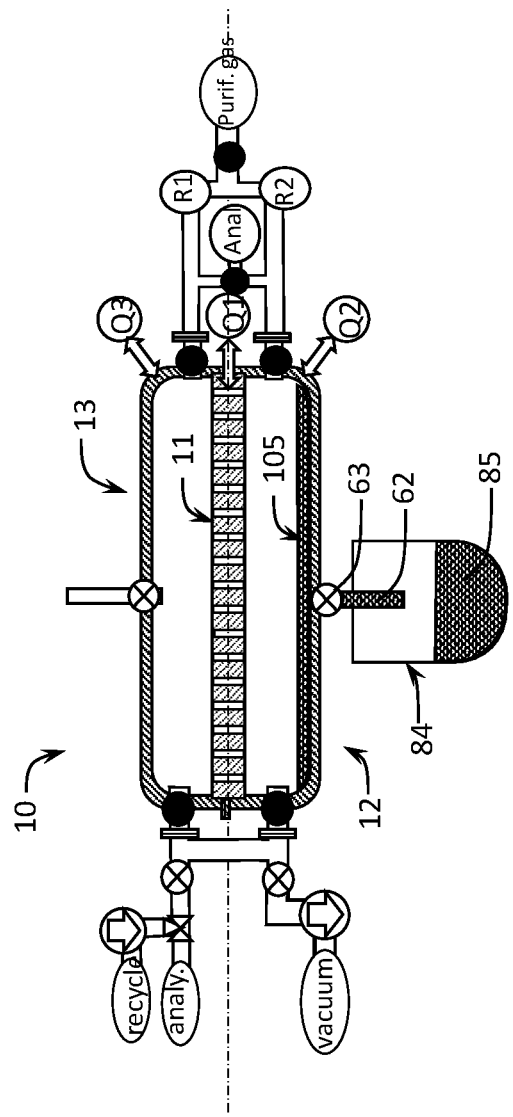
FIG. 18 shows the purified extract material within the vessel of FIG. 8 being dispensed into a single receptacle.

In an alternative embodiment illustrated in FIG. 18, the first chamber vessel 12 is disposed beneath the second chamber vessel 13, and the purified extract material 105 is dispensed from within the lower first chamber vessel 12 through the material port 62, into a storage vessel 84 sized sufficiently to retain the entire charge 85 of the purified extract material 105. The storage vessel 84 can include a sealable cover, to prevent contamination of the charge 85 of the purified extract material 105.

In one embodiment, the funneling tray 26 includes a 7×7 array of tapered surfaces that define through holes 27, as shown in FIG. 12, the array covering a width and length of about 70 mm (about 2.75 inches), each tapered surface having a width and length of about 10 mm (about 0.4 inches). Assuming a layer of extract material of about 4 mm (about 0.16 inches), a volume of about 19.6 cm$^3$ (about 1.2 cubic inches), which is about 20 gms (0.7 ounces) assuming a specific density of 1.

Figure 24:
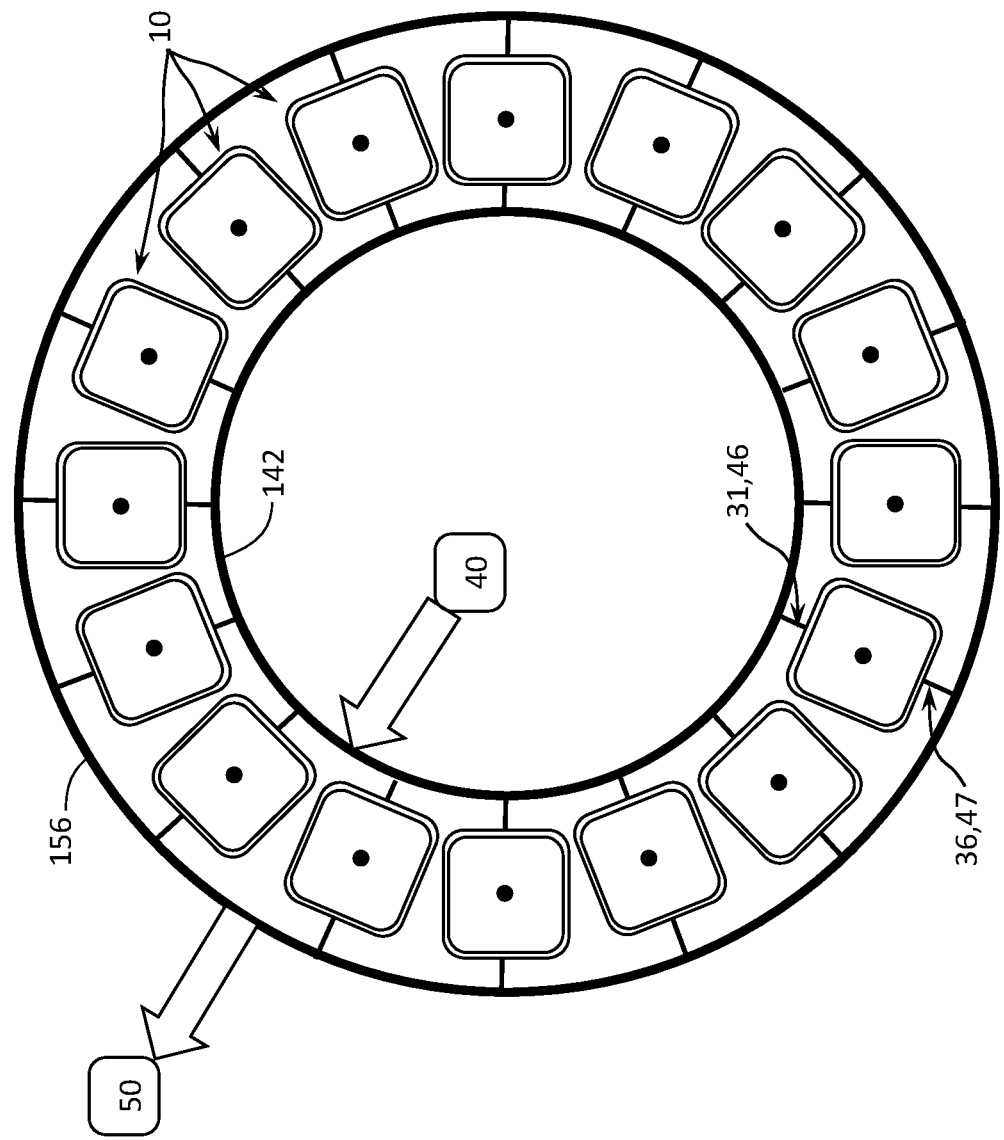
FIG. 24 shows a circular plan view of a plurality of vessels, illustrating a manufacturing-sized prototype design.

FIG. 24 illustrates circular plan view illustrating a plurality of vessels 10, and specifically sixteen vessels, arranged in a circular pattern, and connected to a common manifold for both the gas delivery system 40 and gas recovery system 50. The illustrated embodiment illustrates a concept of a manufacturing-sized prototype design. Each vessel 10 can be as described and illustrated in FIG. 3 and arranged in a circular or other geometric pattern, to support greater production while sharing the gas delivery system 40 and gas recovery system 50 via a common delivery manifold 142 and recovery manifold 156. The plurality of vessels 10 can also be arranged in a line, or in a vertically stacked arrangement, as the need and desire may dictate. Depending on size and arrangement, each vessel 10 individually, or in a group or a whole assembly, can be rotated. The number of vessels 10 in the arrangement can include a number, and each vessel 10 can have the same size or of different scale, as the need and desire may dictate.

Figure 25:
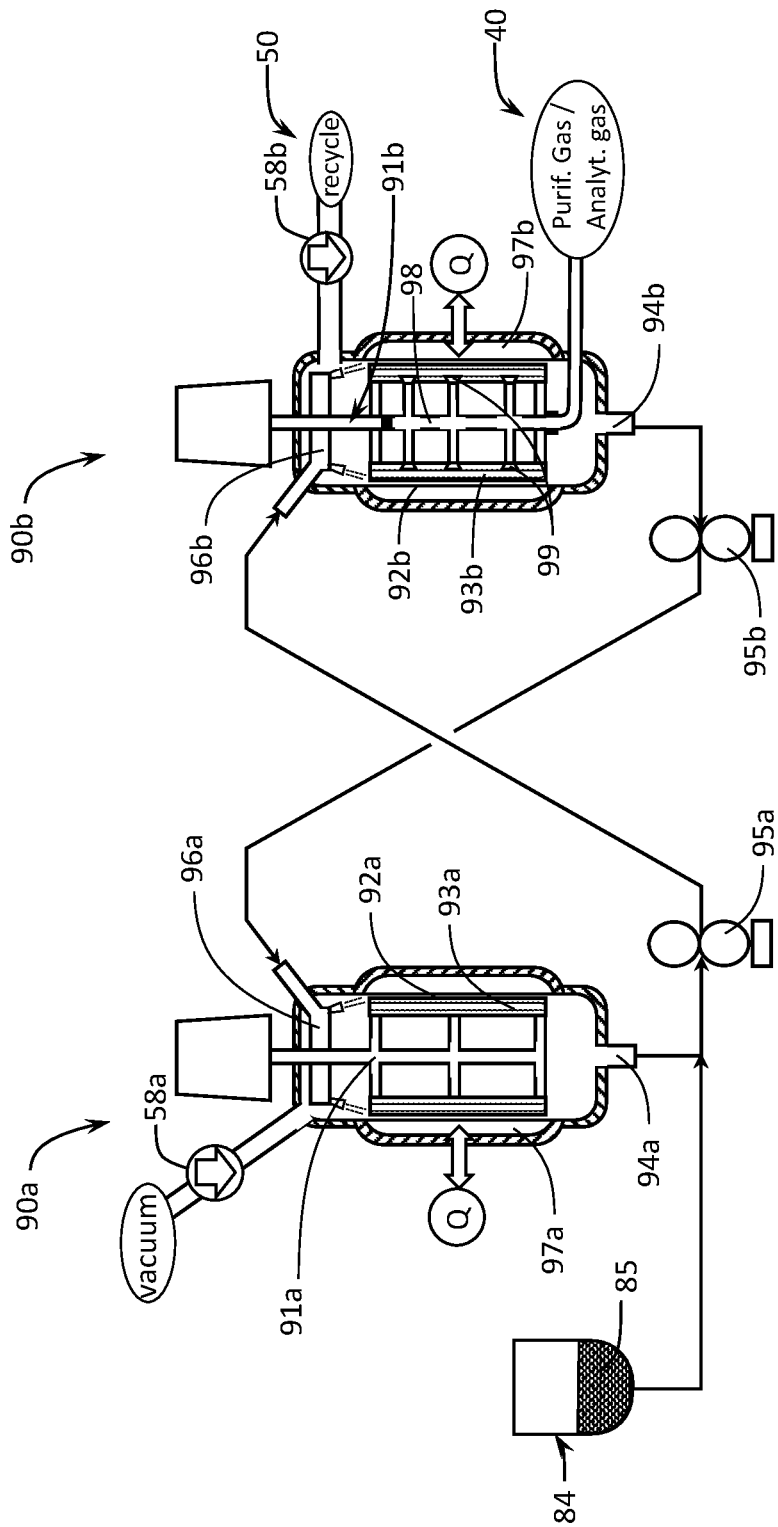
FIG. 25 shows an alternative apparatus and system for use in the process for purifying a cannabinoid extract composition, employing a pair of wiped film evaporators

FIG. 25 illustrates an alternative system and apparatus for use in a process for purifying a cannabinoid extract composition by removing one or more volatile extraction solvents or volatile materials (volatile active compound and/or terpenes) from the cannabinoid extract composition. The system includes a pair of wiped film evaporators (WFEs), including a vacuum WFE 90a and a purifying gas WFE 90b. Each WFE includes an internal cylindrical wall 92 of uniform diameter and a plurality of wiper blades 93 that are fixed at the periphery of a motor-driven, axially rotor 91, which revolves the wiper blades 93 around the axis in close proximity to the cylindrical wall 92, typically with the peripheral tip of the blades spaced apart from the cylindrical wall 92 by a narrow clearance, typically of 1 mm, more or less. Each WFE has an upper manifold 96 for delivering a flowable, liquid feed, and a bottom drain port 95 for extracting a processed flowable liquid. A heated jacket 97 heats the outer surface of the cylindrical wall 92 to heat and raise (or maintain) the temperature of the processed liquid.

A charge 85 of a raw extracted material 85 is fed through a first supply pump 95a to an upper manifold 96b of a purifying gas WFE 90b, for delivering flowable extract material onto or along the internal cylindrical wall 92b that is spread by the wiper blades 93b into a thin film of extract material across the cylindrical surface of the internal cylindrical wall 92b. A flow of a purifying gas is passed into the lower end of the WFE 90b from the gas delivery system 40, which passes into the volume space and out the top end of the WFE 90b to a condenser 58b and a gas recovery system 50. The flowing purifying gas passes into a hollow shaft 98 having a plurality of radially-projecting nozzles 99 directed at the interior wall 92b to impinge the purifying gas into the thin, wiped film of extract material. The impinging purifying gas carries off volatilized solvent material or other volatile material being emitted or volatilized from within and through the surface area of the thin, wiped film of extract material that is spread continuously across the cylindrical surface of the internal cylindrical wall 92b. The volatilized solvent material or other volatile material is condensed in condenser 58b and captured, and the residual purifying gas recycled.

A stripped purified extract material collects and passes through the bottom drain 94b, and is fed through a second supply pump 95b to an upper manifold 96a of a vacuum WFE 90a, for delivering flowable extract material onto or along the internal cylindrical wall 92a that is spread by the wiper blades 93a into a thin film of extract material across the cylindrical surface of the internal cylindrical wall 92a. A vacuum is drawn at the upper end of the vacuum WFE 90a, drawing residual gases and volatile compounds from the volume space and out the top end of the vacuum WFE 90a to a condenser 58a (cold trap) upstream of vacuum system. The vacuum space within the vacuum WFE 90a is exposed to the wiped film of the extract material, to carry off volatilized solvent material or other volatile material being emitted or volatilized from within and through the surface area of the thin film of extract material that is spread continuously across the cylindrical surface of the internal cylindrical wall 92a. The volatilized solvent material or other volatile material drawn off by the vacuum is condensed in condenser 58a and captured.

A first-stage purified extract material collects in the bottom of vacuum WFE 90a and passes through the bottom drain 94a, and back through the second supply pump 95b, to begin a second and subsequent stages of stripping and purifying of the extract material.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

We claim:

1. A dual-chamber vessel including:
   (i) a first chamber vessel and a second chamber vessel, each of the first chamber vessel and the second chamber vessel comprising a peripheral wall having a distal rim that defines an opening into the respective chamber vessel, and a base wall that defines a closed end of the respective chamber vessel, wherein the first chamber vessel and a second chamber vessel can be sealed together along the respective distal rims to form a pressure and vacuum-sealed vessel; and
   (ii) a porous partition that divides the vessel between the first chamber vessel and the second chamber vessel, the porous partition comprising a rigid structure having a multiplicity of passages extending between the opposed outer faces of the porous partition, which passage place the first chamber and the second chamber into fluid communication;
   wherein each of the first chamber vessel and the second chamber vessel include at least one port disposed in either or both the peripheral sidewall and base wall, and at least one shutoff valve to selectively open and close the at least one port.

2. An apparatus comprising:
   (a) a dual-chamber vessel according to claim 1;
   (b) a gas delivery system that includes a supply of a pressurized purifying gas, and associated piping, valving and control devices, for each of the first chamber vessel and a second chamber vessel, independently or jointly, for shutting off and turning on the pressurized purifying gas, and regulating the mass flow rate, the pressure, and the temperature of the pressurized purifying gas, that flows through the respective chamber vessel;
   (c) a gas recovery system that includes (I) a collection and recycle system for a low-pressure gas, including a low-pressure solvent-laden purifying gas, and associated piping, valving and control devices, for each of the first chamber vessel and a second chamber vessel, independently or jointly, for closing off and passing the low-pressure solvent-laden purifying gas, and a condenser to capture condensable fluids from the low-pressure solvent-laden purifying gas, and (II) a vacuum system that communicates fluidly with each of the first chamber vessel and a second chamber vessel, independently or jointly, and associated piping, valving and control devices, and a condenser to capture condensable fluids from the vacuum flow; and (d) a means for rotating the vessel around a central axis in order to switch the respective positions of the first chamber vessel and the second chamber vessel.

3. A manufacturing apparatus comprising:
a) a plurality of dual-chamber vessels according to claim 1, arranged in a pattern;
b) a means for rotating each vessel around a central axis in order to switch the respective positions of the first chamber vessel and the second chamber vessel;
c) a common manifold for a gas delivery system in fluid communication with each of the plurality of vessels; and
d) a common manifold for a gas recovery system in fluid communication with each of the plurality of vessels.

4. The dual-chamber vessel according to claim 1, wherein the vessel is configured to withstand both vacuum and pressure conditions.

5. The dual-chamber vessel according to claim 4, wherein the vessel includes at the first and second chamber vessels are of the same size and dimensions.

6. The dual-chamber vessel according to claim 5, wherein the respective rims of the first and second chambers include a peripheral flange that defines a peripheral seal between the respective open ends of the first chamber vessel and the second chamber vessel.

7. The dual-chamber vessel according to claim 6, wherein the first chamber vessel and the second chamber vessel are positionable manual or robotically, and are controlled manually or automatically.

8. The dual-chamber vessel according to claim 1, wherein the vessel includes at least one material port disposed in the base wall of at least one of the first chamber vessel and the second chamber vessel, for introducing a fluid material into, or withdrawing the fluid material from the vessel.

9. The dual-chamber vessel according to claim 1, wherein the passage is a uniform, straight-through passageway having a diameter or equivalent cross-section size of at least 1 micron, and not more than 2 mm.

10. The dual-chamber vessel according to claim 1, wherein the porous partition comprises a plurality of stacked plates, each plate have a plurality of pores, wherein overlapping pores of the plurality of stacked plates form a corresponding passageway.

11. The dual-chamber vessel according to claim 10, wherein the material of the insert port is aluminum or stainless steel.

12. The dual-chamber vessel according to claim 1, wherein the porous partition includes a plurality of insert ports, each insert port comprising a cylindrical wall, each insert port inserted through and secured within one of the plurality of passageways, to provide a through passage.

13. The dual-chamber vessel according to claim 2, wherein the insert port further includes one or more interior walls that extend along an axial length of the cylindrical wall that subdivide the through passage into two or more sub-passages.

14. The dual-chamber vessel according to claim 13, wherein the material of the insert port is aluminum or stainless steel.

15. The dual-chamber vessel according to claim 1, wherein the porous partition includes a metal foam partition having a multiplicity of open-cell pores that form an interconnected network.

16. The dual-chamber vessel according to claim 1, further including a funneling tray disposed on surfaces of the porous partition, the funneling tray including a plurality of tapered surfaces that provide a through hole for directing a flowable material toward and into the respective passageways with which the through holes are aligned.

17. The dual-chamber vessel according to claim 1, wherein the porous partition comprises a heated porous partition including a means for providing heat input into the porous partition, the means comprising an electromotive force, a heat exchange fluid, and an irradiated energy source.

18. The dual-chamber vessel according to claim 17, wherein the heated porous partition further includes a resistive heat element in electrical communication with the electromotive force.

19. The dual-chamber vessel according to claim 18, wherein the resistive heat element comprises a plurality of horizontally-aligned resistive heat elements extending along opposite sides of the insert ports.

20. The dual-chamber vessel according to claim 17, wherein the first chamber vessel and the second chamber vessel are independently heated with a heat source.

21. An apparatus of claim 2 wherein the means for rotating includes a mechanized apparatus for rotating the vessel around a central axis, and configured for manual or automated control, and wherein the connections between the gas delivery system and the gas recovery system with the vessel are selected from the group consisting of:
(a) quick-connection couplings that mate and connect the respective ports of the vessel with the piping of the gas delivery system and the gas recovery system, to facilitate disconnecting, rotating, and reconnecting the vessel, and
(b) flexible lengths of vacuum/pressure tubing to facilitate rotation of the vessel without having to disconnect the couplings of the tubing with the respective ports of the vessel.

* * * * *

UNITED STATES PATENT AND TRADEMARK OFFICE
CERTIFICATE OF CORRECTION

PATENT NO. : 10,717,056 B1
APPLICATION NO. : 16/565053
DATED : July 21, 2020
INVENTOR(S) : Michael C. Gokay et al.

Page 1 of 1

It is certified that error appears in the above-identified patent and that said Letters Patent is hereby corrected as shown below:

In the Claims

Claim 13, Column 20, Line 68, delete "claim 2" and insert --claim 12--.

Signed and Sealed this
Eighth Day of September, 2020

Andrei Iancu
*Director of the United States Patent and Trademark Office*